(12) United States Patent
Bowen et al.

(10) Patent No.: US 6,310,064 B1
(45) Date of Patent: Oct. 30, 2001

(54) ARALKYL DIAZABICYCLOALKANE DERIVATIVES FOR CNS DISORDERS

(75) Inventors: Wayne Bowen, Derwood; Brian R. de Costa, Rockville; Celia Dominguez, Gaithersburg; Xiao-Shu He, Derwood; Kenner C. Rice, Bethesda, all of MD (US)

(73) Assignee: The United States of America as represented by the of Department of Health and Human Services, Washington, DC (US)

( * ) Notice: Subject to any disclaimer, the term of this patent is extended or adjusted under 35 U.S.C. 154(b) by 0 days.

(21) Appl. No.: 09/347,659

(22) Filed: Jul. 6, 1999

Related U.S. Application Data

(62) Division of application No. 08/954,284, filed on Oct. 20, 1997, now Pat. No. 5,958,920, which is a division of application No. 08/348,654, filed on Dec. 2, 1994, now Pat. No. 5,679,679, which is a continuation of application No. 08/259,203, filed on Jun. 13, 1994, now abandoned, which is a continuation of application No. 07/950,358, filed on Sep. 24, 1992, now abandoned.

(51) Int. Cl.[7] .................. C07D 471/04; C07D 487/04; A61K 31/4985; A61P 25/18
(52) U.S. Cl. .................. 514/249; 544/230; 544/231; 544/349
(58) Field of Search .................. 514/249, 300, 514/393, 221; 546/121; 544/349, 230, 231; 548/302.7; 540/500, 523

(56) References Cited

U.S. PATENT DOCUMENTS

| | | | |
|---|---|---|---|
| 3,531,485 | * 9/1970 | Freed | 260/268 |
| 4,204,003 | 5/1980 | Szmuszkovicz | 424/324 |
| 4,414,389 | * 11/1983 | Freed | 544/349 |
| 4,463,013 | 7/1984 | Collins et al. | 424/274 |
| 4,801,604 | 1/1989 | Von Voightlander | 514/429 |

FOREIGN PATENT DOCUMENTS

| | | |
|---|---|---|
| 2029185 | * 12/1971 | (DE) . |
| 2141464 | * 3/1972 | (DE) . |
| 1125112 | * 8/1968 | (GB) . |
| WO 92/12128 | 7/1992 | (WO) . |

OTHER PUBLICATIONS

Shukla, U. K.; Khanna, J. M.; Sharma,Satyavan; Anand, Nitya; Chatterjee, R. K.; Sen, A. B., Indian J. Chem., Sect. B, 22B(7), 664–8 (English) 1983.*
Alan Lourie and Allan Day, J. Med. Chem., 9, 1966, 311–315.*
Meier Freed and Allan Day, JOC, 25, 1960, 2408–2413.*
Valls, Nativitat; Segarra, Victor M.; Maillo, Luisa C.; Bosch, Joan, Tetrahedron, 47(6), 1065–74 (English) 1991.*
Alan Lourie and Allan Day, J. Med. Chem., 9, 1966, 311–315.*

Diafi, Lahcen; Couquelet, Jacques; Tronche, Pierre; Gardette, Daniel; Gramain, Jean Claude, J. Heterocycl. Chem., 27(7), 2181–7 (English) 1990.*
Meier Freed and Allan Day, JOC, 25, 1960, 2408–2413.*
Aram et al., J. Pharmacol. Exp. Ther., 248, 320–328 (1989) (Abstract).
Bailey et al. Eur. J. Pharmacol., 240, 243 (1993) (Abstract).
Bellville, Clin. Pharm. Ther., 9, 142 (1968).
Canoll et al., J. Neurosci. Res., 24, 311–328 (1989) (Abstract).
Carter et al., J. Pharm Exp. Ther., 247(3), pp 1222–1232 (1988).
Chouinard, Psychopharmacology, 84, 282 (1984).
Clissold, J. Pharm. Exp. Therapeutics, 265, 876 (1993).
Contreras et al., Brain Res., 546, 79–82 (1991).
Cook et al., J. Pharmacol. Exp. Ther., 263, 1159–1166 (1992) (Abstract).
De Costa et al., J. Med. Chem., 32(8), 1996–1002 (1989).
De Costa et al., J. Med. Chem., 35(1), 38–47 (1992).
De Costa, Brain Res., 671, 45 (1995).
De Costa, J. Med. Chem., 35, 4334 (1992).
De Costa, J. Med. Chem, 36, 2311 (1993).
DeCoster et al., Brain Res., 671, 45–53 (1995) (Abstract).
DeHaven–Hudkins et al., Life Sci., 56, 1571–1576 (1995) (Abstract).
Forrest, Clin. Pharm. Ther., 10, 468 (1969).
Gewirtz, Neuropsychopharmacology, 10, 37–40 (1994).
Giardina, Biosystemi Come Targets Farmacologici Recettori Peptidergici, 21–63 (1992).

(List continued on next page.)

Primary Examiner—Mukund J. Shah
Assistant Examiner—Thomas C McKenzie
(74) Attorney, Agent, or Firm—Leydig, Voit & Mayer, Ltd.

(57) ABSTRACT

Certain aralkyl diazabicycloalkyl compounds are disclosed for treatment of CNS disorders, such as cerebral ischemia, psychosis, and convulsions.

For example, compounds of interest are of the formula:

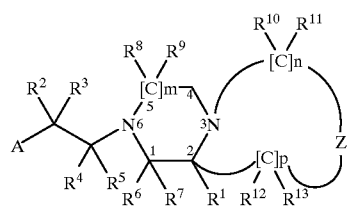

21 Claims, No Drawings

OTHER PUBLICATIONS

Gilman et al., *The Pharmacological Basis of Therapeutics*, 7th Edition, 404 (1985).
Goldberg, *J. Pharm. Exp. Ther.*, 243, 784 (1987).
Gonzalez et al., *J. Pharm Exp. Therapeutics*, 271, 212 (1994).
Gonzalez–Alvean, *Brain Res.*, 673, 61 (1995).
Hadkins, *Life Sci.*, 49 p1229 (1992).
Hudkins et al., *Life Sci.*, 49(17), 1229–1235 (1991).
Itzhak et al., *FASEB J.*, 3, 1868–1872 (1989).
Izhak et al., *Acedemic Press*, 191–204 (1994).
Kirk et al., *J. Pharmacol. Exp. Ther.*, 271, 1080–1085 (1994) (Abstract).
Klein et al., *J. Pharmacol. Exp. Ther.*, 260, 990–999 (1992) (Abstract).
Klein et al., *Eur. J. Pharmacol.*, 254, 239–248 (1994).
Lasage et al., *Synapse*, 20, 156–64 (1995) (Abstract).
Lason et al., *Brain Res.*, 482, 333–339 (1989).
Lobner, *Neurosci Letters*, 117, 169 (1990).
Long et al., *Soc. Neurosci. Abs.*, 16, 1122, abstract 461.4 (1990).
Loscher et al., *Eur. J. Pharmacol.*, 238, 191–200 (1993).
Lysko et al., *Stroke*, 23, 1319–1323 (1992) (Abstract).
Lysko et al., *Stroke*, 23, 414–419 (1992) (Abstract).
Parsons et al., *Neuropharm.*, 25(2), 217–220 (1986).
Pontecorvo, *Brain Res. Bulletin*, 26, 461–465 (1991).
Radesca et al., *J. Med. Chem.*, 34(10), 3058–3065 (1991).
Ragowski, *Drugs*, 44, 279 (1992).
Ragowski, *J. Pharm. Exp. Therepeutics*, 259, 30 (1991).
Ragowski, *TIPS*, 14, 325 (1993).
Reddy et al., *J. Med. Chem.*, 37, 260–267 (1994) Abstract only.
Rees, *Biosystemi Come Targets Farmacologici Recettori Peptidergici*, 65–101 (1992).
Ronsisvale, *Biosystemi Come Targets Farmacologici Recettori Peptidergici*, 102–133 (1992).
Roth et al., *Eur. J. Pharmacol.*, 236, 327–331 (1993).
Rothman et al., *Annals of Neurology*, 19(2), 105–111 (1986).
Scopes et al., *J. Med. Chem.*, 35, 490–501 (1992).
Simon, *Science*, 226, 850 (1984).
Takahashi et al., *Stroke*, 26, 1676–1682 (1995) (Abstract).
Tortella et al., *Trends Pharmacol. Sci.*, 10, 501–507 (1990).
Tortella et al., *Trends Pharmacol. Sci.*, 11, 146–147 (1990).
Walker, *Clin. Neuropharmacology*, 12, 322 (1989).
Weissman et al., *Biol. Psych.*, 29, 41–54 (1991).
Weissman et al., *Biol. Psychiatry*, 29, 41–54 (1991).
Witkin et al., *J. Pharmacol. Exp. Ther.*, 266, 473–482 (1993).

* cited by examiner

ARALKYL DIAZABICYCLOALKANE DERIVATIVES FOR CNS DISORDERS

CROSS-REFERENCE TO RELATED APPLICATIONS

The present invention is a divisional of application Ser. No. 08/954,284, filed on Oct. 20, 1997, now issued as U.S. Pat. No. 5,958,920 which was a divisional of application Serial No. 08/348,654, filed on Dec. 2, 1994, now issued as U.S. Pat. No. 5,679,679, which was a continuation of application Ser. No. 08/259,203 filed Jun. 13 1994 now abandoned which was a continuation of application Ser. No. 07/950,358 filed on Sep. 24, 1992, now abandoned,

FIELD OF THE INVENTION

This invention is in the field of clinical neurology and relates specifically to a class of therapeutically useful compounds, compositions and methods for treatment of central nervous system (CNS) dysfunctions, neurotoxic damage, or neurodegenerative diseases. For example, these compounds are particularly useful for treating neurotoxic injury which follows periods of hypoxia, anoxia or ischemia associated with stroke, cardiac arrest or perinatal asphyxia. These compounds are also useful as antipsychotics and anticonvulsants.

BACKGROUND OF THE INVENTION

Unlike other tissues which can survive extended periods of hypoxia, brain tissue is particularly sensitive to deprivation of oxygen or energy. Permanent damage to neurons can occur during brief periods of hypoxia, anoxia or ischemia. Neurotoxic injury is known to be caused or accelerated by certain excitatory amino acids (RAA) found naturally in the central nervous system (CNS). Glutamate (Glu) is an endogenous amino acid which has been characterized as a fast excitatory transmitter in the mammalian brain. Glutamate is also known as a powerful neurotoxin capable of killing CNS neurons under certain pathological conditions which accompany stroke and cardiac arrest. Normal glutamate concentrations are maintained within brain tissue by energy-consuming transport systems. Under low energy conditions which occur during conditions of hypoglycemia, hypoxia or ischemia, cells can release glutamate. Under such low energy conditions the cell is not able to take glutamate back into the cell. Initial glutamate release stimulates further release of glutamate which results in an extracellular glutamate accumulation and a cascade of neurotoxic injury.

It has been shown that the sensitivity of central neurons to hypoxia and ischemia can be reduced by either blockage of synaptic transmission or by the specific antagonism of postsynaptic glutamate receptors [see S. M. Rothman and J. W. Olney, "Glutamate and the Pathophysiology of Hypoxia-Ischemic Brain Damage," *Annals of Neurology*, 19 No. 2 (1986)]. Glutamate is characterized as a broad spectrum agonist having activity at three neuronal excitatory amino acid receptor sites. These receptor sites are named after the amino acids which selectively excite them, namely: Kainate (KA), N-methyl-D-aspartate (NMDA or NMA) and quisqualate (QUIS).

Neurons which have EAA receptors on their dendritic or somal surfaces undergo acute excitotoxic degeneration when these receptors are excessively activated by glutamate. Thus, agents which selectively block or antagonize the action of glutamate at the EAA synaptic receptors of central neurons can prevent neurotoxic injury associated with hypoxia, anoxia, or ischemia caused by stroke, cardiac arrest or perinatal asphyxia.

It is known that compounds of various structures, such as aminophosphonovalerate derivatives and piperidine dicarboxylate derivatives, may act as competitive antagonists at the NMDA receptor. Certain piperidineethanol derivatives, such as ifenprodil and 1-(4-chlorophenyl)-2-[1-(4-fluorophenyl)-piperidinyl]ethanol, which are known antiischemic agents, have been found to be non-competitive NMDA receptor antagonists [C. Carter et al, *J. Pharm Exp. Ther*, 247 (3), 1222–1232 (1988)].

There are many classes of compounds known for treatment of psychotic disorders. For example, current therapeutic treatments for psychoses use compounds classifiable as phenothiazine-thioxanthenes, as phenylbutylpiperidines and also as certain alkaloids. An example of a phenylbutylpiperidine compound of current use in psychotic treatment therapy is haloperidol [A. F. Gilman et al, *The Pharmacological Basis of Therapeutics*, 7th Edn., p. 404, MacMillan (1985)].

Certain nitrogen-containing cyclohetero cycloalkylaminoaryl compounds are known for pharmaceutical purposes. For example, U.S. Pat. No. 4,204,003 to Szmuszkovicz describes N-(2-aminocyclopentyl)-N-alkanoylanilides as antidepressant agents.

Certain aminocycloaliphatic benzamides have been described for various uses. For example, U.S. Pat. No. 4,463,013 to Collins et al describes aminocyclohexylbenzamides for use as diuretic agents. The compound (±)-trans-3,4-dichloro-N-methyl-N-[2-(1-pyrrolidinyl)cyclohexyl)-benzeneacetamide has been evaluated for its selectivity as an amino acid antagonist [C. G. Parsons et al, *Neuropharm.*, 25(2), 217–220 (1986)]. This same compound has been evaluated for its neuroprotective activity against kainate-induced toxicity [W. Lason et al, *Brain Res.*, 482, 333–339 (1989)]. U.S. Pat. No. 4,801,604 to Vonvoightlander et al describes certain cis-N-(2-aminocycloaliphatic) benzamides as anticonvulsants including, specifically, the compound cis-3,4-dichloro-N-methyl-N-[2-(1-pyrrolidinyl)cyclohexyllbenzamide. Certain of these trans benzeneacetamide derivatives, such as trans-3,4-dichloro-N-methyl-N-[2-(1-pyrrolidinyl)cyclohexyl]-benzeneacetamide, have been described as highly selective ligands for kappa opioid receptors. The cis isomers of 3,4-dichloro-N-methyl-N-[2-(1-pyrrolidinyl)cyclohexyl]-benzeneacetamide were identified to be potent and selective sigma ligands [B. R. de Costa et al, *J. Med. Chem.*, 32(8), 1996–2002 (1989)]. Further structure activity studies with these compounds resulted in the identification of (+)- and (−)-cis-N-[3,4-dichlorophenylethyl]-N-methyl-2-(1-pyrrolidinyl)-cyclohexylamines as extremely potent and selective ligands for the sigma receptor. These [Contreras, P. C.; Ragan,.D. M.; Bremer, M. E.; Lanthorn, T. H.; Gray, N. M.; Iyengar, S.; Jacobson, A. E. ; Rice, K. C. ; de Costa, B. R.: Evaluation of U50488H analogs for antiischemic activity in the gerbil. *Brain Res.* 1991, 546, 79–82] and related (ethylenediamines) compounds [Long, J. B.; Tortella, F. C.;

Rice, K. C.; de Costa B. R.: Selective sigma ligands protect against dynorphin A-induced spinal cord injury in rats. *Soc. Neurosci. Abs.*, 16, 1122 (1990) abs 461.4] were found to be effective as-protective agentsfor the damaging effects of ischemia and stroke in two different models of ischemia. See, for example, Long, J. B.; Tortella, F. C.; Rice, K. C.; de Costa B. R.: Selective sigma ligands protect against dynorphin A-induced spinal cord injury in rats. *Soc. Neurosci. Abs.*, 16, 1122 (1990) abs 461.4; Contreras, P. C.; Ragan, D. M.; Bremer, M. E.;

Lanthorn, T. H.; Gray, N. M.; Iyengar, S.; Jacobson, A. E.; Rice, K. C.; de Costa, B. R.: Evaluation of U50488H analogs for antiischemic activity in the gerbil. *Brain Res.* 1991, 546, 79–82. Since these initial findings, neuroprotective activity has been identified among certain other high affinity sigma ligands. It is likely that the protective effects of these and related compounds is mediated through their interaction with the sigma receptor. Scopes et al., *J. Med. Chem.*, 35, 490–501 (1992) describe certain 2-[(alkylamino)methyl]-piperidines. In particular, 1-[(3,4-dichlorophenyl)acetyl]-2 [(alkylamino)methyl]piperidines are described as having activities as kappa opioid receptor agonists.

BRIEF DESCRIPTION OF THE INVENTION

Treatment of CNS disorders and diseases such as cerebral ischemia, psychotic disorders and convulsions, as well as prevention of neurotoxic damage and neurodegenerative diseases, may be accomplished by administration of a therapeutically-effective amount of a compound of the formula:

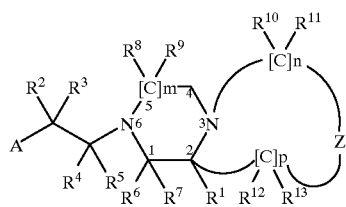

wherein each of $R^1$, $R^4$, $R^5$, $R^6$ and $R^7$ is independently selected from hydrido, alkyl, cycloalkyl, cycloalkylalkyl, aralkyl, aryl, alkoxyalkyl, haloalkyl, hydroxyalkyl, carboxy, carboxyalkyl, alkanoyl, alkenyl and alkynyl;
wherein each of $R^2$, $R^3$ and $R^8$ through $R^{13}$ is independently selected from hydrido, hydroxy, alkyl, cycloalkyl, cycloalkylalkyl, aralkyl, aryl, alkoxy, aryloxy, aralkoxy, alkoxyalkyl, haloalkyl, hydroxyalkyl, cyano, amino, monoalkylamino, dialkylamino, carboxy, carboxyalkyl, alkanoyl, alkenyl and alkynyl; wherein $R^2$ and $R^3$ may be taken together to form oxo or to form a saturated or partially unsaturated carbocyclic group having three to eight ring carbons; wherein $R^4$ and $R^5$ may be taken together to form a saturated or partially unsaturated carbocyclic group having three to eight ring carbons; wherein $R^8$ and $R^9$ may be taken together to form oxo; wherein $R^{10}$ and $R^{11}$ may be taken together to form oxo; wherein m is an integer from 2–4 and n and p are integers of from one to four;

wherein is selected from

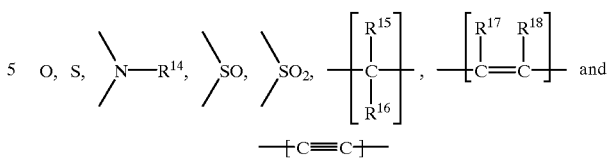

wherein $R^{14}$ may be selected from hydrido, alkyl, cycloalkyl, cycloalkylalkyl, aryl, aralkyl, heteroaryl, alkanoyl, aralkanoyl, aroyl, aminoalkyl, monoalkylaminoalkyl and dialkylaminoalkyl; wherein each of $R^{15}$ and $R^{16}$ is independently selected from hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, amino, monoalkylamino, dialkylamino, carboxy, carboxyalkyl and alkanoyl; wherein each of $R^{17}$ and $R^{18}$ is independently selected from hydrido, alkyl, cycloalkyl, cycloalkylalkyl, aralkyl, alkoxyalkyl, haloalkyl, hydroxyalkyl, halo, cyano, carboxy, carboxyalkyl and alkanoyl; wherein A is selected from aryl, heteroaryl, aryloxy, heteroaryloxy, aralkoxy, heteroaralkoxy, arylamino, heteroarylamino, aralkylamino, heteroaralkylamino, arylthio, heteroarylthio, aralkylthio and heteroaralkylthio; wherein any of the foregoing A groups can be further substituted with one or more substituents independently selected from hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, cyano, amino, monoalkylamino, dialkylamino, carboxy, carboxyalkyl, alkanoyl, alkenyl and alkynyl; or a pharmaceutically-acceptable salt thereof A preferred family of compounds of Formula I consists of those compounds wherein each of $R^1$, $R^4$, $R^5$, $R^6$ and $R^7$ is independently selected from hydrido, alkyl, cycloalkyl, cycloalkylalkyl, aralkyl, arylalkoxyalkyl, haloalkyl, hydroxyalkyl, carboxy, carboxyalkyl, alkanoyl, alkenyl and alkynyl; wherein each of $R^2$, $R^3$ and $R^8$ through $R^{13}$ is independently selected from hydrido, hydroxy, alkyl, cycloalkyl, cycloalkylalkyl, aralkyl, aryl, alkoxy, aryloxy, aralkoxy, alkoxyalkyl, haloalkyl, hydroxyalkyl, cyano, amino, monoalkylamino, dialkylamino, carboxy, carboxyalkyl, alkanoyl, alkenyl and alkynyl; wherein $R^2$ and $R^3$ may be taken together to form oxo or to form a saturated or partially unsaturated carbocyclic group having three to eight ring carbons; wherein $R^4$ and $R^5$ may be taken together to form oxo or to form a saturated or partially unsaturated-carbocyclic group having three to eight ring carbons; wherein $R^{10}$ and $R^{11}$ may be taken together to form oxo; wherein m is an integer from 2–4 and n and p are integers of from one to four;
wherein Z is selected from

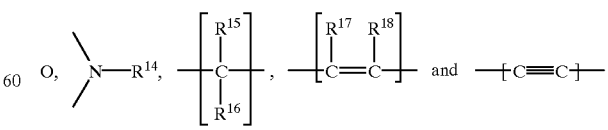

wherein $R^{14}$ may be selected from hydrido, alkyl, cycloalkyl, cycloalkylalkyl, aryl, aralkyl, heteroaryl, alkanoyl, aralkanoyl and aroyl; wherein each of $R^{15}$ through $R^{18}$ is independently selected from hydrido, alkyl, cycloalkyl, cycloalkylalkyl, aralkyl, aryl, alkoxyalkyl, haloalkyl, hydroxyalkyl, halo, cyano, carboxy, carboxyalkyl and alkanoyl; wherein A is selected from aryl, heteroaryl, aryloxy, heteroaryloxy, aralkoxy, heteroaralkoxy, arylamino, heteroarylamino, aralkylamino, heteroaralkylamino, arylthio, heteroarylthio, aralkylthio and heteroaralkylthio; wherein any of the foregoing A groups can be further substituted with one or more substituents independently selected from hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, cyano, amino, monoalkylamino, dialkylamino, carboxy, carboxyalkyl, alkanoyl, alkenyl and alkynyl; or a pharmaceutically acceptable salt thereof.

A more preferred family of compounds within Formula I consists of those compounds wherein each of $R^1$, $R^4$, $R^5$, $R^6$ and $R^7$ is independently selected from hydrido, loweralkyl, cycloalkyl of three to about eight carbon atoms, phenylloweralkyl, phenyl, loweralkoxyloweralkyl, halolow-eralkyl; hydroxyloweralkyl, carboxy, carboxyloweralkyl, loweralkanyl, loweralkenyl, loweralkynyl; wherein $R^2$, $R^3$ and $R^8$ through $R^{13}$ is independently selected from hydrido, hydroxy, loweralkyl, cycloalkyl of three to about eight carbon atoms, cycloalkylalkyl of four to about eight carbon atoms, phenylloweralkyl, phenyl, loweralkoxy, phenoxy, phenylloweralkoxy, loweralkoxyloweralkyl, haloloweralkyl, hydroxyloweralkyl, cyano, amino, monoloweralkylamino, diloweralkylamino, carboxy, carboxyloweralkyl, loweralkanoyl, loweralkenyl and loweralkynyl; wherein $R^2$ and $R^3$ may be taken together to form a saturated or partially unsaturated carbocyclic group having three to eight ring carbons; wherein $R^4$ and $R^5$ may be taken together to form a saturated or partially unsaturated carbocyclic group having three to eight ring carbons; wherein $R^{10}$ and $R^{11}$ may be taken together to form oxo; wherein m is an integer from 2–4 and n and p are integers of from one to four; N wherein Z is selected from

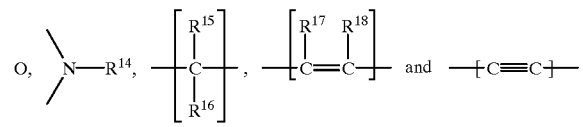

wherein $R^{14}$ may be selected from hydrido, loweralkyl, cycloalkyl of three to about eight carbon atoms, cycloalkylalkyl of four to about eight carbon atoms, phenyl, phenylloweralkyl, heteroaryl, loweralkanoyl, phenylalkanoyl, benzoyl, aminoloweralkyl, monoloweralkyl-aminoloweralkyl and diloweralkylamino-loweralkyl; wherein each of $R^{15}$ and $R^{16}$ is independently selected from hydrido, hydroxy, loweralkyl, cycloalkyl of three to about eight carbon atoms, cycloalkylalkyl of four to about eight carbon atoms, phenylloweralkyl, phenyl, loweralkoxyloweralkyl, haloloweralkyl, hydroxyloweralkyl, halo, cyano, amino, monoloweralkylamino, diloweralkylamino, carboxy, carboxyloweralkyl and loweralkanoyl; wherein each-of $R^{17}$ and $R^{18}$ is independently selected from hydrido, loweralkyl, cycloalkyl of three to about eight carbon atoms, cycloalkylalkyl of four to about eight carbon atoms, phenylloweralkyl, phenyl, loweralkoxyloweralkyl, haloloweralkyl, hydroxyloweralkyl, halo, cyano, carboxy, carboxyloweralkyl and loweralkanoyl; wherein A is selected from phenyl, naphthyl, heteroaryl, phenoxy, naphthyloxy, heteroaryloxy, phenylloweralkoxy, naphthylloweralkoxy, heteroarylloweralkoxy, phenylamino, naphthylamino, heteroarylamino; phenylloweralkylamino, naphthylloweralkylamino, heteroaralkylamino, phenylthio, naphthylthio, heteroarylthio, phenylloweralkylthio and heteroarylloweralkylthio; wherein any of the foregoing A groups can be further substituted with one or more substituents independently selected from hydrido, hydroxy, loweralkyl, cycloalkyl of three to about eight carbon atoms, cycloalkylalkyl of four to about eight carbon atoms, phenylloweralkyl, phenyl, loweralkoxy, phenoxy, phenylloweralkoxy, loweralkoxyloweralkyl, halo, haloloweralkyl, hydroxyloweralkyl, cyano, amino, monoloweralkylamino, diloweralkylamino, carboxy, carboxyloweralkyl, loweralkanoyl, loweralkenyl and loweralkynyl; or a pharmaceutically acceptable salt thereof.

A more highly preferred family of compounds of Formula I consists of those compounds wherein each of $R^1$, $R^4$, $R^5$, $R^6$ and $R^7$ is independently selected from hydrido, loweralkyl, cycloalkyl of three to about eight carbon atoms, cycloalkylalkyl of four to about eight carbon atoms, benzyl, phenyl, loweralkoxyloweralkyl, haloloweralkyl, hydroxyloweralkyl, loweralkanoyl, loweralkenyl, and loweralkynyl; wherein $R^2$, $R^3$ and $R^8$ through $R^{13}$ is independently selected from hydrido, hydroxy, loweralkyl, cycloalkyl of three to about eight carbon atoms, cycloalkylalkyl of four to about eight carbon atoms, benzyl, phenyl, loweralkoxy, phenoxy, benzyloxy, loweralkoxyloweralkyl, haloloweralkyl, hydroxyloweralkyl, loweralkanoyl, loweralkenyl and loweralkynyl; wherein $R^2$ and $R^3$ may be taken together to form a saturated or partially unsaturated carbocyclic group having three to eight ring carbons; wherein $R^4$ and $R^5$ may be taken together to form a saturated or partially unsaturated carbocyclic group having three to eight ring carbons; wherein $R^{10}$ and $R^{11}$ may be taken together to form oxo; wherein m is an integer from 2–4 and n and p are integers of from one to four; wherein Z is selected from

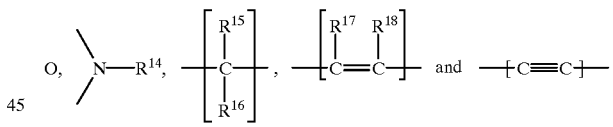

wherein $R^{14}$ may be selected from hydrido, loweralkyl, cycloalkyl of three to about eight carbon atoms, cycloalkylalkyl of four to about eight carbon atoms, phenyl and benzyl; wherein each of $R^{15}$ through $R^{18}$ is independently selected from hydrido, loweralkyl, cycloalkyl of three to about eight carbon atoms, cycloalkylalkyl of four to about eight carbon atoms, benzyl, phenyl, loweralkoxyloweralkyl, hydroxyloweralkyl and halo; wherein A is selected from phenyl, naphthyl, benzo[b]thienyl, thienyl, phenoxy, benzyloxy, naphthyloxy, thiophenoxy, phenylamino, benzylamino, naphthylamino, phenylthio, benzylthio and naphthylthio; wherein any of the foregoing A groups can be further substituted with one or more substituents independently selected from hydrido, hydroxy, loweralkyl, cycloalkyl of three to about eight carbon atoms, cycloalkylalkyl of four to about eight carbon atoms, loweralkoxy, loweralkoxyloweralkyl, halo, haloloweralkyl, hydroxyloweralkyl, amino, monoloweralkylamino, diloweralkylamino, loweralkanoyl, loweralkenyl and loweralkynyl; or a pharmaceutically acceptable salt thereof.

A family of compounds of particular interest within Formula I are compounds embraced by Formula II:

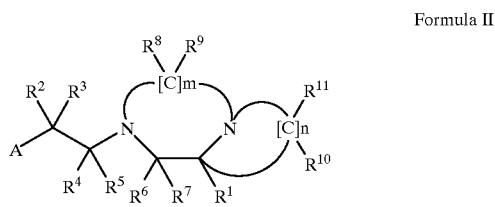

Formula II wherein each of $R^1$, $R^4$, $R^5$, $R^6$ and $R^7$ is independently selected from hydrido, loweralkyl, benzyl and halolower-alkyl; wherein $R^2$, $R^3$ and $R^8$ through $R^{11}$ is independently selected from hydrido, hydroxy, loweralkyl, benzyl, phenoxy, benzyloxy and haloloweralkyl; wherein n is an integer of from four to six; wherein m is, an integer of from two to four; wherein A is selected from phenyl, naphthyl, benzothienyl, benzofuranyl and thienyl; wherein any of the foregoing A groups can be further substituted with one or more substituents independently selected from hydrido, hydroxy, loweralkyl, loweralkoxy, halo, haloloweralkyl, amino, monoloweralkylamino and diloweralkylamino; or a pharmaceutically acceptable salt thereof.

A more preferred family of compounds within Formula II consists of compounds wherein each of $R^1$, $R^4$, $R^5$, $R^6$ and $R^7$ is independently selected from hydrido, methyl, ethyl, propyl, benzyl, and haloloweralkyl, wherein $R^2$, $R^3$ and $R^8$ through $R^{11}$ is independently selected from hydrido, hydroxy, methyl, ethyl, propyl, benzyl, phenoxy, benzyloxy and haloloweralkyl; wherein n is a number selected from 4 or 5; wherein m is an integer of from two or three; wherein A is phenyl or naphthyl; wherein any of the foregoing A groups can be further substituted with one or more substituents independently selected from hydroxy, methyl, ethyl, propyl, methoxy, ethoxy, methylenedioxy, halo, trifluoromethyl, amino, methylamino and dimethylamino; or a pharmaceutically acceptable salt thereof.

Of highest interest are the following specific compounds:
2-[2-(3,4-dichlorophenyl)ethyl]-2,5-diazabicyclo[3.0.4] nonane
2-[2-(3-benzothienyl)ethyl]-2,5-diazabicyclo[3.0.4]nonane
2-[2-naphthylethyl]-2,5-diazabicyclo(3.0.4]nonane
2-[2-(3,4-dichlorophenyl)ethyl]-2,5-diazabicyclo[4.0.4] decane
2-[2-(3-benzothienyl)ethyl]-2,5-diazabicyclo[4.0.4]decane
2-[2-naphthylethyl]-2,5-diazabicyclo[4.0.4]decane The term "hydrido" denotes a single hydrogen atom (H) which may be attached, for example, to an oxygen atom to form hydroxyl group. Where the term "alkyl" is used, either alone or within other terms such as "haloalkyl" and "hydroxyalkyl", the term "alkyl" embraces linear or branched radicals having one to about twenty carbon atoms or, preferably, one to about ten carbon atoms. More preferred alkyl radicals are "lower alkyl" radicals having one to about five carbon atoms. The term "cycloalkyl" embraces cyclic radicals having three to about six carbon atoms, such as cyclopropyl and cyclobutyl. The term "haloalkyl" embraces radicals wherein any one or more of the alkyl carbon atoms is substituted with one or more halo groups, preferable selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. An example of a polyhaloalkyl is a trifluoromethyl group. The terms "alkylol" and "hydroxyalkyl", embrace linear or branched alkyl groups having one to about ten carbon atoms any one of which may be substituted with one or more hydroxyl groups. The term "alkenyl" embraces linear or branched radicals having two to about twenty carbon atoms, preferably two to about ten carbon atoms, and containing at least one carbon-carbon double bond. The term "alkynyl" embraces linear or branched radicals having two to about twenty carbon atoms, preferably two to about ten carbon atoms, and containing at least one carbon-carbon triple bond. The terms "cycloalkenyl" and "cycloalkynyl" embrace cyclic radicals having three to about ten ring carbon atoms including, respectively, one or more double or triple bonds involving adjacent ring carbons. The terms "alkoxy" and "alkoxyalkyl" embrace linear or branched oxy-containing radicals each having alkyl portions of one to about ten carbon atoms, such as methoxy group. The "alkoxy" or "alkoxyalkyl" radicals may be further substituted with one or more halo atoms, such as fluoro, chloro or bromo, to provide haloalkoxy or haloalkoxyalkyl groups. The term "heteroaryl" embraces aromatic ring systems containing one or two hetero atoms selected from oxygen, nitrogen and sulfur in a ring system having five or six ring members, examples of which are thienyl, furanyl, pyridinyl, thiazolyl, pyrimidyl and isoxazolyl including benz-fused systems such as benzothienyl, 2-quinolinyl and the like. The term "alkylene chain" describes a chain of two to six methylene (—CH$_2$—) groups which may form a cyclic structure with or without a hetero atom in the cyclic structure.

Specific examples of alkyl groups are methyl, ethyl, n-propyl, isopropyl, n-butyl, sec-butyl, iso-butyl, tert-butyl, n-pentyl, iso-pentyl, methyl-butyl, dimethylbutyl and neo-pentyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

Included within the family of compounds of Formulas I–II are the tautomeric forms of the described compounds, isomeric forms including enantiomers and diastereoisomers, and the pharmaceutically-acceptable salts thereof. The term "pharmaceutically-acceptable salts" embraces salts commonly used to form alkali metal salts and to form addition, salts of free acids or free bases. Since the compounds of Formulas I–II contain basic nitrogen atoms, such salts are typically acid addition salts. The phrase "pharmaceutically-acceptable salts" is not intended to embrace quaternary ammonium salts. The nature of the salt is not critical, provided that it is pharmaceutically acceptable, and acids which may be employed to form salts are, of course, well known to those skilled in this art. Examples of acids which may be employed to form pharmaceutically acceptable acid addition salts include such inorganic acids as hydrochloric acid, sulfuric acid and phosphoric acid, and such organic acids as maleic acid, succinic acid and citric acid other pharmaceutically acceptable salts include salts with alkali metals or alkaline earth metals, such as sodium, potassium, calcium and magnesium, or with organic bases, such as dicyclohexylamine. All of these salts may be prepared by conventional means by reacting, for example, the appropriate acid or base with the corresponding compound of Formulas I–II in a suitable solvent (e. g. methanol).

GENERAL SYNTHETIC PROCEDURES

Compounds of Formulas I and II may be prepared in accordance with the following generic procedures, within which specific schemes are shown for Formula II type compounds.

Step 1

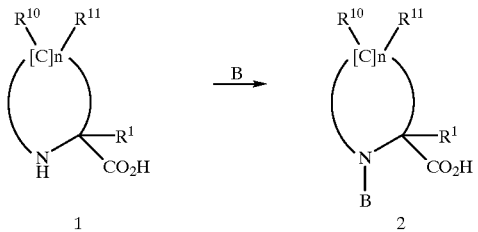

wherein $R^1$, $R^{10}$ through $R^{11}$, and n are as defined previously; and wherein B represents a protecting group such as acetyl, benzoyl, t-butyloxycarbonyl or benzyloxycarbonyl.

A process for preparing the compounds of the invention starts with carboxylic acid derivatives of cycloaminoalkyl compounds of general structure 1 where $R^1$, $R^{10}$ through $R^{11}$, and n have the value assigned previously. Examples of compounds within the general structure 1 are the enantiomers of proline (2-pyrrolidinecarboxylic acid) and 2-piperidinecarboxylic acid. The amino group of 1 is protected employing protecting groups such as acetyl, benzoyl, t-butoxycarbonyl or benzyloxycarbonyl or other amino protecting groups familiar to those skilled in the art. This protection can be achieved by reacting the protecting group as the chloride or anhydride in organic solvents and at temperatures ranging from −60° to reflux of the reaction mixture.

Step 2

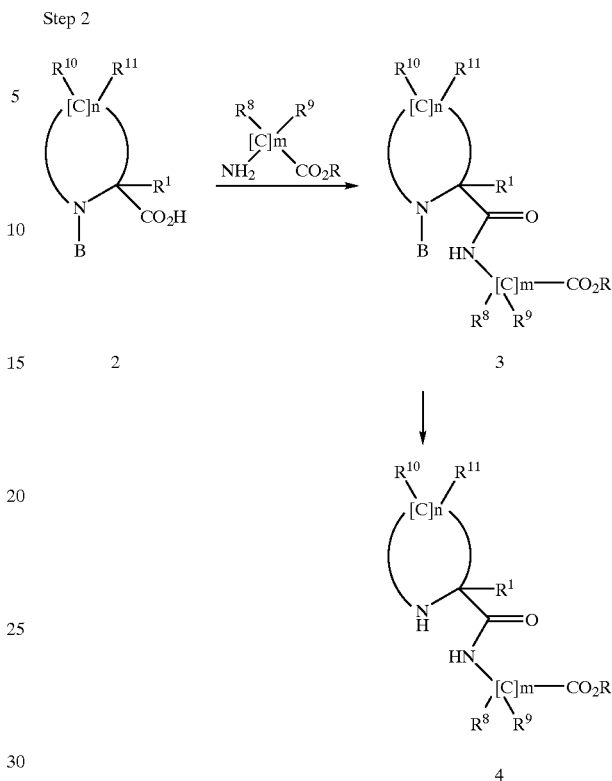

wherein B, $R^1$, $R^8$, $R^9$, $R^{10}$, $R^{11}$, n, and m are as defined previously, and R is a carboxyl protecting group, e.g. R is methyl.

In the second step of the process, compounds of the general structure 2 are coupled by way of the carboxylic acid group to a carboxy-protected amino acid of the formula:

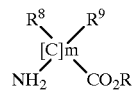

Examples of amino acids include glycine, t-butyl glycine, β-amino butyric acid and the like. The compounds can be combined neat or in a variety of solvents such as tetrahydrofuran. Following isolation of 3, the protecting group B is removed by methods well known to those skilled in the art. The amino protecting group B is removed by mixing 3 with a suitable acid such as trifluoroacetic acid, hydrochloric acid, and the like which are familiar to those skilled in the art. Alternatively, the amino protecting group is removed by mixing 3 with a suitable base such as sodium hydroxide, potassium hydroxide and the like, which are familiar to those skilled in the art. The compounds are mixed in a suitable solvent, preferably a protic solvent such as water, ethylene glycol, or methanol. Alternatively, in the case of the benzyloxycarbonyl group, deprotection can be achieved by catalytic hydrogenation in the presence of a suitable catalyst such as 10% palladium on carbon in a suitable solvent such as methanol. The temperature of the reaction can vary from room temperature to reflux of the reaction mixture. For example, treatment of a stirred mixture of 2, a methyl ester hydrochloride of an α- amino acid (1.0 molar equivalent), 1-(dimethylaminopropyl)-3-(ethyl)carbodiimide hydrochloride (1.2 molar equivalents) and N-hydroxybenzotriazole (1 molar equivalents) with triethylamine (2 molar equivalents) afforded 3. This was isolated by standard methods familiar to those skilled in the art. The product 3 was dissolved in trifluoroacetic acid and the solution was stirred for one hour. The product 4 was isolated by evaporation of the trifluoroacetic acid in vacuo. The temperature of the reaction can vary from room temperature to reflux of the reaction mixture.

Step 3

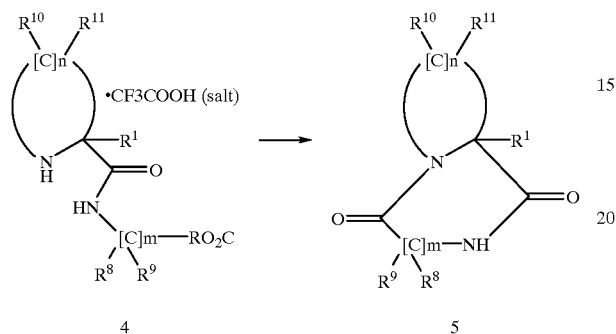

wherein $R^1$, $R^8$, $R^9$, $R^{10}$, $R^{11}$ and m and n are as defined previously. In the third step of the process, compounds of general structure 4 are cyclized to bicyclic compounds of general structure 5 by dissolving trifluoroacetic acid salts of general structure A in methanol, treating with triethylamine and refluxing the mixture until the cyclization is complete. The resulting product 5 is a diketo diazabicycloalkane.

Step 4 wherein $R^1$, $R^8$, $R^9$, $R^{10}$, $R^{11}$, m, and n are as defined previously.

In the fourth step of the process, the diketo diazabicycloalkanes of general structure 5 are reduced to diazabicycloalkanes of general structure 6 by reducing the amide moieties. The reduction can be accomplished by employing reducing agents well known to those skilled in

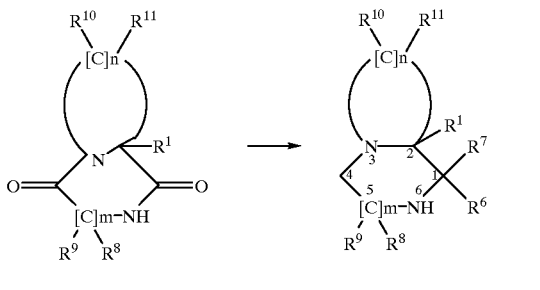

the art, such as, for example, employing lithium aluminum hydride, aluminum hydride, sodium borohydride. The reaction can be conducted in either protic or aprotic solvents, depending on the reducing agent of choice. The temperature of the reaction can vary from room temperature to reflux of the reaction mixture.

Step 5

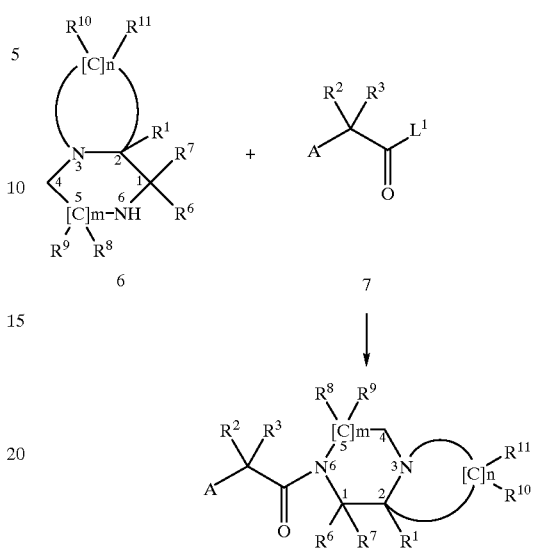

wherein A, $R^1$, $R^2$, $R^3$, $R^8$ through $R^{11}$, m and n are as defined previously; and wherein $L^1$ is a good leaving group such as chloro, bromo, acyloxy, or. "activated" hydroxy. In the fifth step of the process, diazabicycloalkanes of general structure 6 are converted to amides of general structure 8 where A, $R^2$, and $R^3$ have the value assigned previously and $L^1$ is a good leaving group such as chloro, bromo, acyloxy, or "activated" hydroxy. The conversion can be best achieved by mixing the reagents neat or in a protic solvent such as tetrahydrofuran, methylene chloride, or ether in the presence of a base such as triethylamine. The reaction can be run in the absence or presence of an activating agent such as dicyclohexylcarbodiimide or phosphorus oxychloride, depending on the leaving group of choice. The temperature of the reaction can vary from 0° to reflux of the reaction mixture.

Step 6

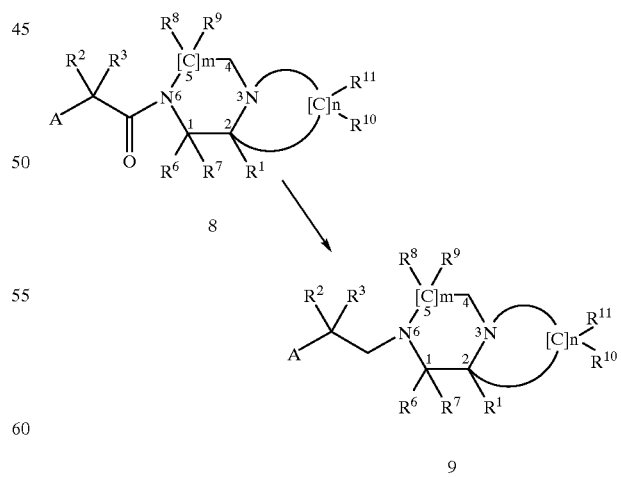

wherein A, $R^1$, $R^2$, $R^3{}_1$, $R^8$ through $R^{11}$, m and n are as defined previously.

In the sixth step of the process, amides of general structure 8 are converted to amines of general structure 9 by employing reducing agents such as lithium aluminum hydride, aluminum hydride, sodium borohydride, sodium cyanoborohydride, or other reducing agents familiar to those skilled in the art. This reduction can be accomplished in either protic or aprotic solvents, depending on the reducing agent of choice, and at temperatures ranging from room temperature to reflux of the reaction mixture.

Step 6(b)

Alternately, amines of general structure 11 can be prepared according to the following generic procedure.

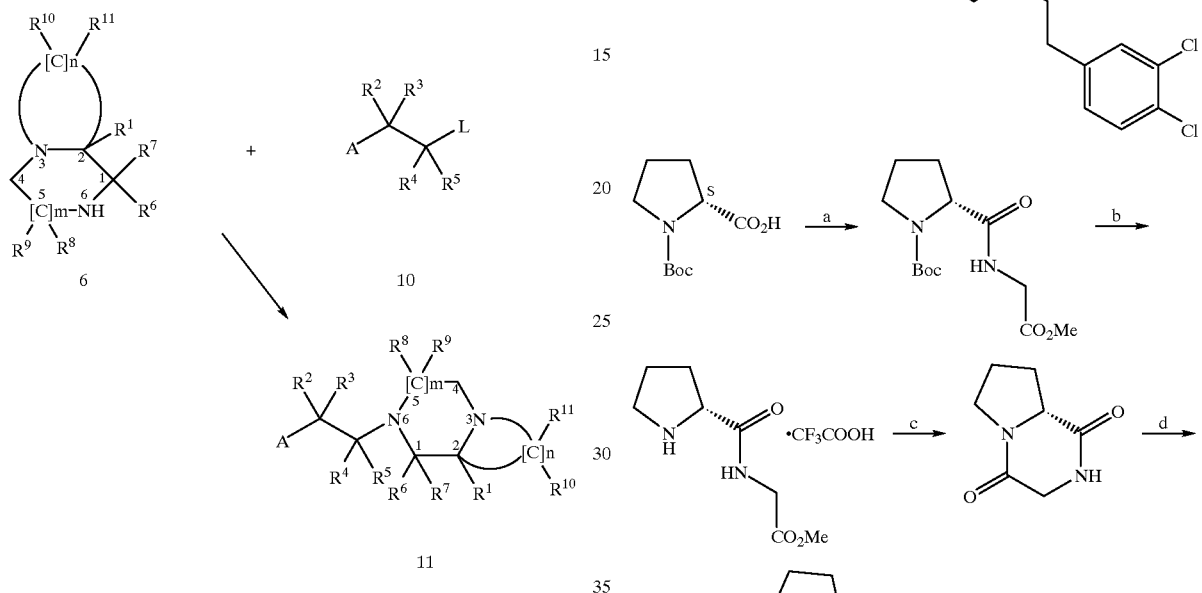

wherein A, $R^1$ through $R^{11}$ and m and n are as defined previously; and wherein $L^2$ is a good leaving group such as halogen, tosylate, mesylate, or brosylate.

Amines of general structure 11 can be alternately prepared by combining compounds of general structure 6 with compounds of general structure 10 where A, $R^1$ through $R^{11}$, m and n have the values assigned previously and where $L^2$ is a good leaving group such as halogen, tosylate, mesylate, or brosylate. The compounds can be combined in a variety of solvents such as toluene, xylenes, dimethylformamide, hexamethylphosphoramide, or ethanol. The temperature of the reaction can vary from room temperature to reflux of the reaction mixture.

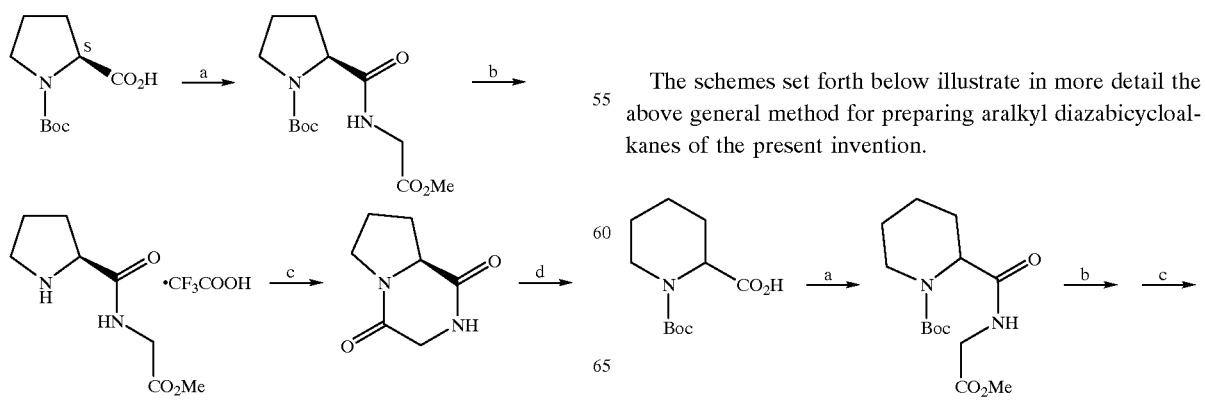

The schemes set forth below illustrate in more detail the above general method for preparing aralkyl diazabicycloalkanes of the present invention.

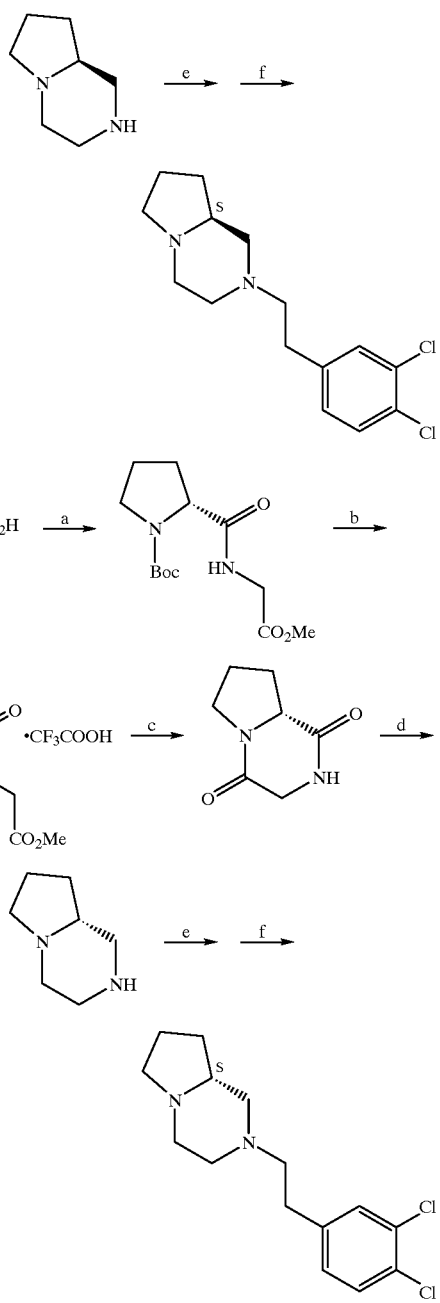

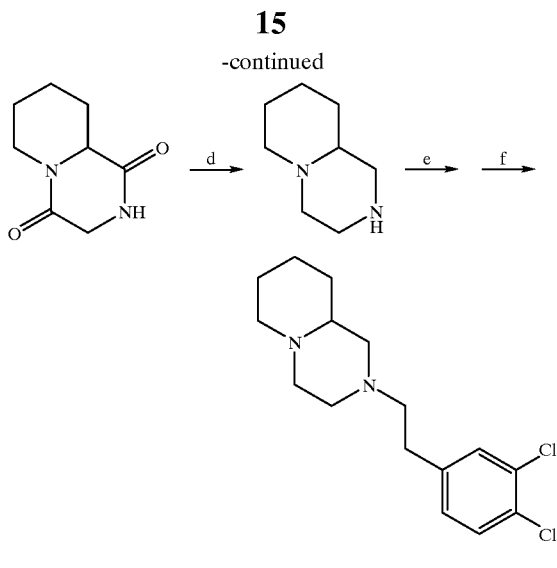

a: 1-(dimethylaminopropyl)-3-(ethyl)carbodiimide.hydrochloride, HOBT, glycine methyl ester, Et$_3$N, r.t.; b: CF$_3$COOH; c: MeOH, Et$_3$N, reflux; d: LiAlH$_4$, THF, reflux; e: 3,4-dichlorophenylacetic acid, DCC, CH$_2$Cl$_2$, r.t.; f: AlH$_3$ THF, r.t.

The following Examples are detailed descriptions of the methods of preparation of compounds of Formula I. These detailed preparations fall within the scope of, and serve to exemplify, the above described Generic Procedures which form part of the invention. These Examples are presented for illustrative purposes only and are not intended as a restriction on the scope of the invention. All parts are by weight unless otherwise indicated. Most of the commercially available starting materials were obtained from Aldrich Chemical Company, Milwaukee, Wis.

Melting points were determined on a Thomas-Hoover capillary apparatus and are uncorrected., Specific rotation determinations at the sodium-D line were obtained in a 1 dM cell using a Perkin-Elmer 241-MC polarimeter. Elemental analyses were performed at Atlantic Microlabs, Atlanta, Ga. Chemical-ionization mass spectra (CIMS) were obtained using a Finnigan 1015 mass spectrometer. Electron ionization mass spectra (EIMS) and high resolution mass measurements (HRMS). were obtained using a VG-Micro Mass 7070F mass spectrometer. $^1$H-NMR spectra were measured from,CDCl$_3$ solutions using a Varian SL-300 spectrometer. Thin layer chromatography (TLC) was performed on 250 μM Analtech GHLF silica gel plates. TLC system A corresponds to CHCl$_3$-MeOH-conc. aq. NH$_3$ (90:9:1). TLC system B corresponds to CHCl3-MeOH-conc. aq. NH$_3$ (80:18:2). TLC system C corresponds to EtOAc/hexanes (1:2). No attempt was made to optimize the yields. For purposesof clarity, enantiomeric compounds are indicated with prefixes indicating absolute configuration and/or the direction of rotation whereas racemic compounds are shown without prefixes.

EXAMPLE 1

Preparation of (S)-Glycine methyl ester-N-(tertbutoxycarbonyl)prolinamide

To a stirred mixture of Boc-L-proline (5.0 g, 23 mmol), glycine methyl ester hydrochloride (2.92 g, 23 mmol, 1.0 eq), 1-(dimethyl-aminopropyl)-3-(ethyl)carbodiimide hydrochloride (5.34 g, 27.9 mmol, 1.2 eq) and HOBT (3.77 g, 33. 5 mmol, 1 eq) was added Et$_3$N (6.5 mL, 47 mmol, 2.0 eq) and the reaction mixture was stirred for 24 h at rt when TLC (solvent system C) indicated the reaction to be complete. The solvent was evaporated in vacuo and the residue was taken up in EtOAc (200 mL) and washed successively with water (200 mL), 5% aqueous citric acid (4×60 mL), 10% aqueous K$_2$CO3 (2×100 mL) and the solvent was evaporated in vacuo to give the product as a colorless crystalline solid (3.89 g): mp 70–71° C. (EtOAc/isooctane 1:3);

$^1$H-NMR (CDCl$_3$) σ6.54 (br s, 1H, CONH), 4.105 (m, 2H), 3.75 (s, 3H), 3.46 (m, 2H), 2.06–2.44 (m, 2H), 1.91 (m, 3H), 1.47 (s, 9H, tBu); Anal (calcd for C$_{13}$H$_{22}$N$_2$O$_5$): C 54.53, H 7.74, N 9.78. Found: C 54.56, H 7.77, N 9.80.

EXAMPLE 2

Preparation of (S)-(Glycine methyl ester) prolinamide

The title compound of Example 1 (2.6 g, 9.1 mmol) was dissolved in CF$_3$COOH (10 mL) and the solution was stirred at rt for 1 h when TLC (solvent system A) indicated the reaction to be complete. The reaction solvent was evaporated in vacuo to give a colorless oil (quantitative). Conditions were maintained sufficiently cold (4° C.) and the base was isolated by partitioning between cold saturated K$_2$CO$_3$ solution and CHCl$_3$. The product was sufficiently stable for analysis by $^1$H-NMR spectroscopy. For purposes of further characterization, the oxalate salt was crystallized from 2-propanol: mp 119–120° C.

$^1$H-NMR (CDCl$_3$) σ8.09 (br s, 1H, CONH), 4.04 (d, J=5.9 Hz, 2H), 3.78 (dd, J=5.1, 9.0 Hz, 1H), 3.75 (s, 3H), 2.90–3.08 (m, 2H), 2.07–2.21 (m, 1H), 1.89–2.01 (m, 1H), 1.61–1.83 (m, 2H), 1.63 (br s, 1H, NH); Anal (calcd for C$_{10}$H$_{16}$N$_2$O$_7$): C 43.48, H 5.84, N 10.14. Found: C 43.63, H 5,55, N 9:97.

EXAMPLE 3

Preparation of (S)-1,4-Diketo-2,5-diazabicyclo[3.0.4]nonane

The CF$_3$COOH salt of the title compound of Example 2 was dissolved in MeOH (50 mL) and treated with Et$_3$N (5.0 mL). The reaction mixture was boiled under reflux overnight or until complete by TLC (solvent system A). The solvent was evaporated in vacuo and the oily residue was dissolved in hot 2-propanol (20 mL). Crystallization occurred spontaneously on cooling to rt to give the desired product (0.91 g, 65%): mp 211–213° C.

$^1$H-NMR (CDCl$_{13}$) σ6.41 (br s, 1H, NH), 4.10 (d, J$_{gem}$= 16 Hz, 2H), 3.89 (dd, J$_{gem}$=17 Hz, J=4.4 Hz, 1H), 3.51–3.71 (complex m, 2H), 2.39 (m, 1H), 1.82–2.17 (complex m, 3H); Anal (calcd for C$_7$H$_{10}$N$_2$O$_3$): C 54.54, H 6.54, N 18.17. Found: C 54.73, H 6.47, N 18.26.

EXAMPLE 4

Preparation of (S)-2,5-Diazabicyclo[3.0.4]nonane

The title compound of Example 3 (0.91 g) in dry THF was added dropwise at ambient temperature to a stirred solution of LiAlH$_4$ in THF (24 mL of a 1.0 M solution, 24 mmol). The reaction mixture was stirred at ambient temperature and then treated dropwise with water (0.9 mL), 15% aqueous NaOH (0.9 mL), and finally water (2.7 mL). The mixture was stirred for 1 h and filtered. The filter-cake was washed with a little cold THF (10 mL) and the combined filtrate and washings were evaporated in vacuo to give the desired product as a colorless oil. Treatment of a solution of the base in EtOH/2-propanol (1:1) with 48% HBr gave the HBr salt: (1.04 g, 67%) as colorless crystals: mp 234–236;

$^1$H-NMR (CDCl$_3$) σ2.92–3.16 (complex m, 4H), 2.84 (m, 1H), 2.48 (m, 1H), 2.06–2.18 (m, 2H), 1.64–1.90 (complex m, 4H), 1.24–1.45 (m, 1H); Anal (calcd for C$_7$H$_{16}$Br$_2$N$_2$): C 29.19, H 5.60, N 9.73. Found: C 29.29; H 5.54, N 9.66.

EXAMPLE 5

Preparation of (S)-2-(3,4-Dichlorophenylacetyl)-2,5-diazabicyclo[3.0. 41nonane

The HBr salt of the title product of Example 4 (1.00 g, 3.3 mmol) and 3,4-dichlorophenylacetic acid (1.07 g, 5.2 mmol, 1.5 eq) and DCC (1.43 g, 6.9 mmol, 2.0 eq) were reacted by addition of Et$_3$N (2.4 mL, 5.0 eq) to give the title -compound (0.84 g, 92%) as a colorless crystalline solid. The reaction was-conducted as follows. To a stirred solution of the dichlorophenylacetic acid in CH$_2$Cl$_2$ (100 mL) was added a solution of the DCC in CH$_2$Cl$_2$ (100 mL) and the solution was stirred for 10 min at rt. To the precipitated complex was added the salt of the title compound of Example 4 followed by the Et$_3$N and stirring was continued until TLC (solvent system A) indicated the reaction to -be complete. The precipitated DCU was removed by filtration and the filter cake was washed with Et$_2$0 (50 mL). The filtrate was diluted with enough Et$_2$0 to render the organic layer less dense than the aqueous layer, and the organic extract was then extracted with 10% aqueous -citric acid (200 mL) and discarded. The aqueous layer was washed with Et$_2$0 (2×200 mL) and the combined washings were discarded. The aqueous layer was basified by addition of excess concentrated aqueous NH$_3$ solution and extracted with CH$_2$Cl$_2$ (2×200 mL). The combined organic layer was washed with water, dried (Na$_2$SO$_4$) and evaporated to give the desired product: mp 102.5–103.5° C. 2-propanol);

$^1$H-NMR (CDCl$_3$) σ7.39 (d, J=7.9 Hz, 1H), 7.35 (d, J=2.0 Hz, 1H), 7.09 (d, J=2.0, 7.9 Hz, 1H), 4.67 (dd, J$_{gem}$=39 Hz, J=13 Hz, 1H), 3.81 (dd, J$_{gem}$=44, J=13 Hz, 1H), 3–68 (d, J=3.8 Hz, 2H), 2.73–3.28 (complex m, 3H), 1.98–2.48 (complex m, 3H), 1.64–1.93 (complex m, 4H), 1.32–1.48 (m, 1H); Anal (calcd for C$_{15}$H$_{18}$Cl$_2$N$_2$O): C 57.52, H 5.79, N 8.94. Found: 57.60, H 5.76, N 8.94.

EXAMPLE 6

Preparation of (S)-2-[2-(3,4-Dichlorophenyl)ethyl]-2,5-diazabicyclo[3.0.41nonane The title compound of Example 5 (0.5 g, 1.60 mmol) was reduced with 0.667 M AlH$_3$ in THF (12 mL, 8.0 mmol,. 5 eq) by adding the Example 5 title compound dropwise to freshly prepared AlH$_3$ solution. TLC (solvent system A) indicated the reaction to be complete after 20 min at rt. The reaction mixture was poured into 15% aqueous NaOH (100 mL) and the solution was extracted with CHCl$_3$ (200 mL). The organic layer was dried by filtration through a column of Na$_2$SO$_4$ and the solvent was evaporated in vacuo to give the title compound as a colorless oil. The HBr salt crystallized from EtOH (0.50 g, 68%): mp 261.5–262.5° C. (dec).

$^1$H-NMR (CDCl$_3$) σ7.34 (d, J=8.3 Hz, 1H), 7.30 (d, J=2.0 Hz, 1H), 7.04 (dd, J=2.0, 8.3 Hz, 1H), 3.00–3.12 (complex m, 3H), 2.89 (dm, J=7.8 Hz, 1H), 2.73–2.81 (m, 2H), 2.58–2.67 (m, 2H), 2.30 (d, J=7.6 Hz, 2H), 2.00–2.22 (complex m, 2H), 1.68–1.98 (complex m, 4H), 1.42 (m, 1H); Anal (calcd for C$_{15}$H$_{22}$Br$_2$Cl$_2$N$_2$: C 39.08, H 4.81, N 6.08. Found: C 39.16, H 4.76, N 5.98.

EXAMPLE 7

Preparation of (R)-Glycine methyl ester-N-(tert-butoxycarbonyl)prolinamide

The title compound was synthesized as described above in Example 1 for its enantiomer starting with Boc-D-proline (5.0 g, 23 mmol) to give 2.39 g of thereof as a colorless crystalline solid identical to the title compound of Example 1: mp 70–71° C.;

Anal (calcd for C$_{13}$H$_{22}$N$_2$O$_5$): C 54.53, H 7.74, N 9.78. Found : C 54.42, H 7.73, N 9.84.

EXAMPLE 8

Preparation of Glycine methyl esterprolinamide

The title compound of Example 7 (2.00 g) was converted to the CF$_3$COOH salt of the N-deprotected product (quantitative) as described above -for its enantiomer. For the purposes of further characterization, the oxalate salt was crystallized from 2-propanol: mp 119–120° C.

The $^1$H-NMR (CDCl$_3$) was identical to that of S-30above. Anal (calcd for C$_{10}$H$_{16}$N$_2$O$_7$):C 43.48, H 5.84, N 10.14. Found: C 54.67, H 6.58, N 18.18.

EXAMPLE 9

Preparation of (R)-1,4-Diketo-2,5-diazabicyclo-[3.0.4]nonane

The CF$_3$COOH salt of the title compound of Example 8 was cyclized as described above for its enantiomer to give 0.68 g, 64% of product mp211° C.;

$^1$H-NMR (CDCl$_3$) identical to its enantiomer above; Anal (calcd for C$_7$H$_{10}$N$_2$O$_2$): C 54.54, H 6.54, N 18.17. Found: C 54.67, H6.58, N 18.18.

EXAMPLE 10

Preparation of (R)-2,5-Diazabicyclo[3.0.4]nonane

The product of Example 9 (0.50 g) was reduced with 15 mL of a 1.0 M LiAlH$_4$ in THF as described in Example 4 to give 0.63 g, 68% of the desired product: mp 234–236° C. (MeOH);

$^1$H-NMR (CDCl$_3$) identical to its enantiomer; Anal (calcd for C$_7$H$_{16}$ Br$_2$N$_2$): C 29.19, H 5.60, N 9.73. Found: C 29.25, H 5.61, N 9.69

EXAMPLE 11

Preparation of (R)-(3,4-Dichlorophenylacetyl)-2,5-diazabicyclo[3.0.4]nonane

The HBR salt of the title compound of Example 10 (0.50 g) was coupled with 3,4-dichlorophenylacetic acid as described in Example 5 to give the desired product (0.51 g, 94%): mp 101–102° C. (2-propanol);

$^1$H-NMR (CDC$_{l3}$) identical to its enantiomer above; Anal (calcd for C$_{15}$H$_{18}$Cl$_2$N$_2$O): C 57.52, H 5.79, N 8.94. Found: C 57.53, H 5.81, N 8.89.

EXAMPLE 12

Preparation of (R)-2-[2-(3,4-Dichlorophenyl)ethyl]-2,5-diazabicyclo[3.0.4]nonane The title compound of Example 11 (0.425 g) was reduced with 0.667 M AlH$_3$ in THF as described in Example 6 above to give the HBr salt of the title compound 0.30 g (48%): mp 263–265° C. (EtOH);

$^1$H-NMR. (CDC13) identical to its enantiomer above; Anal (calcd for C$_{15}$H$_{22}$Br$_2$C$_{12}$N$_2$): C 39.08, H 4.81, N 6.08. Found: C 39.17, H 4.78, N 6.05.

EXAMPLE 13,

Preparation of Glycine methyl ester-N-(butoxycarbonyl)pipecolinamide 1-(tertButoxycarbonyl)-2-piperidinecarboxylic acid (11.46 g, 1.2 eq), glycine methyl ester hydrochloride (9.42 g), 1-(dimethylaminopropyl)-3-(ethyl)carbodiimide hydrochloride (8.00 g, 1.0 eq) and Et$_3$N (16.3 mL) were reacted as described in Example 1 to give 5.6 g of the title compound as a colorless crystallinesolid: mp 118.5–119.5° C. (EtOAc/isooctane 1:3);

$^1$H-NMR (CDCl3) σ6.60 (br s, 1H, CO$\underline{NH}$), 4.81 (m, 1H), 3.82–4.35 (complex m, 4H), 3.76 (s, 3H, OMe), 2.89 (m, 1H), 2.32 (m, 1H), 1.33–1.72 (complex m, 4H), 1.49 (s, 9H, tBu); Anal (calcd for C$_{14}$H$_{24}$N$_2$O$_5$): C 55.99, H 8.05, N 9.33.Found: C 56.00, H 8.09, N 9.36.

EXAMPLE 14

Preparation of 1,4-Diketo-2,5-diazabicyclo-4.0.4] decane

The title compound of Example 13 (4.60 g) was dissoved in CF$_3$COOH and the solution stirred at rt for 10 min. The solvent was evaporated to give the corresponding N-deprotected amine CF$_3$COOH salt (quantitative). This salt was dissolved in saturated NaHCO$_3$ (50 mL) and the solution was extracted with CHC$_{13}$ (4×200 mL). The combined organic extract was dried (Na$_2$SO$_4$) and the solvent was evaporated in vacuo at rt to give an intermediate as a colorless oil in quantitative yield. For purposes of further characterization, the fumarate of his intermediate was crystallized from EtOAc: mp 116–118° C.

$^1$H-NMR (CDCl$_3$) σ7.29 (br s, 1H, $\underline{NH}$CO), 4.05 (d, J=5.6 Hz, 2H), 3.76 (s, 3H, COO$\underline{Me}$), 3.26 (m, 1H), 3.06 (dm, Jgem=12 Hz, 1H), 2.70 (m, 1H), 1.97 (m, 1H), 1.80 (m, 1H), 1.33–1.67 (complex m, 5H); Anal (calcd for C$_{13}$H$_{20}$N$_2$O$_7$): C 49.36, H 6.37, N 8.86. Found: C 49.22, 146.41, N 8.85.

The fumarate was found to be indefinitely stable unlike its free base. The free base as obtained above was dissolved in MeOH (50 mL) and the solution was boiled under reflux overnight under an argon atmosphere. Evaporation of the solvent in vacuo afforded the desired product as a colorless crystalline solid (quantitative). Crystallization from 2-propanol afforded the title compound as colorless crystals: mp 159–160° C.;

$^1$H-NMR (CDCl$_3$) σ6.11 (br s, 1H, NH), 4.70 (dm, J$_{gem}$=13 Hz, 1H), 4.05 (br s, 2H), 3.85 (dm, J$_{gem}$=11 Hz, 1H), 2.53 (m, 1H), 2.36 (m, 1H), 2.02 (m, 1H), 1.40–1.68 (complex m, 3H); Anal (calcd for C$_8$H$_{12}$N$_2$O$_2$): C 57.13, H 7.19, N 16.66. Found: C 57.23, H 7.17, N 16.70.

EXAMPLE 15

Preparation of 2,5-Diazabicyclo[4.0.4]decane

The title compound of Example 14 (0.80 g) was reduced with 1.0 M LiAlH$_4$ in THF as described in Example 4 to give the desired product (0.63 g, 94%) as a clear colorless oil. The oxalate salt was crystallized from MeOH: mp 178–179° C. (dec).

$^1$H-NMR (CDCl$_3$) σ2.94 (m, 2H), 2.75–2.84 (m, 2H), 2.72 (dm, J=11 Hz, 1H), 2.50 (dd, J=10, 12 Hz, 1H), 2.00–2.20 (complex m, 2H), 1.71–1.89 (complex m, 2H), 1.54–1.69 (complex m, 3H), 1.49 (m, 1H), 1.11–1.38 (complex m, 2H); Anal (calcd for C$_{12}$H$_{20}$N$_2$O$_8$): C 44.98, H 6.29, N 8.75. Found: C 45.11, H 6.31, N 8.80.

EXAMPLE 16

Preparation of 2-(3,4-Dichlorophenylacetyl)-2,5-diazabicyclo[4.0.4]decane

The title compound,of Example 15 base (0.49 g, 3.5 mmol) was coupled with 3,4-dichlorophenylacetic acid (1.07 g, 5.2 mmol) as described in Example 5 to give the amide as a crystalline solid: mp 119–120° C. (2-propanol).

$^1$H-NMR (CDCl$_3$) σ7.39 (d, J=8.3 Hz, 1H), 7.35 (d, J=2.0 Hz, 1H), 7.09 (d, J=8.3 Hz, 1H), 4.48 (m, 1H), 3.66 (br s, 2H), 3.64 (m, 1H), 3.29 and 2.87 (m, 1H), 2.64–2.85 (complex m, 2H), 2.41 and 2.09 (m, 1H), 1.93–2.06 (complex m, 2H), 1.40–1.87 (complex m, 5H), 1.12–1.36 (complex m, 2H); Anal (calcd for C$_{16}$H$_{20}$Cl$_2$N$_2$O): C 58.72, H 6.16, N 8.56. Found: C 58.80, H 6.17, N 8.52.

EXAMPLE 17

Preparation of 2-[2-(3,4-Dichlorophenyl)ethyl]-2,5-diazabicyclo[4.0.4]decane

The amide prepared in Example 16 (0.50 g) was reduced with 0.66 M AlH$_3$ in THF (11.6 mL) as described forin to Example 6 give the HBr salt of the title compound (0.5 g, 69%): mp 272–273° C. (dec) (EtOH).

$^1$H-NMR (CDCl$_3$) s 7.34 (d, J=8.3 Hz, 1H), 7.30 (d, J=2.0 Hz, 1H), 7.04 (dd, J=2.0, 8.3 Hz, 1H), 2.81–2.91 (m, 2H), 2.75 (m, 3H), 2.54 (m, 2H), 2.31 (d, J=8.3 Hz, 2H), 1.86–2.11 (complex m, 3H), 1.48–1.82 (complex m, 5H), 1.16–1.39 (m, 2H); Anal (calcd for C$_{16}$H$_{24}$Br$_2$Cl$_2$N$_2$): C 40.45, H 5.09, N 5.90. Found: C 40.57, H 5.12, N 5.81.

BIOLOGICAL EVALUATION

Radioreceptor Assay

The compounds of Examples 6, 12 and 17 were tested for their ability to displace [$^3$H](+)-pentazocine from guinea pig brain membranes [de Costa et al, *FEBS Lett.*, 251, 53–58, 1989] to determine the relative potency of the compounds interacting with the sigma receptor. Receptor binding assays were performed using the crude synaptosomal ($P_2$) membrane fraction of guinea pig brain.

Crude $P_2$ membrane fractions were prepared from frozen (−80° C.) guinea pig brains (Pel-Freeze, Rogers, Ak.), minus cerebella. After removal of cerebella, brains were allowed to thaw slowly on ice and placed in ice-cold 10 mM Tris-HCl, pH 7.4, containing 320 mM sucrose (Tris-sucrose buffer). Brains were then homogenized in a Potter-Elvehjem homogenizer by 10 strokes of a motor driven Teflon pestle in a volume of 10 mL/g tissue wet weight. The homogenate was centrifuged at 1000 g for 10 min at 4° C., and the supernatants were saved. The pellets were resuspended by vortexing in 2 mL/g ice-cold Tris-sucrose and centrifuged again at 1000 g for 10 min. The combined 1000 g supernatant was centrifuged at 31000 g for 15 min at 4° C. The pellets were resuspended by vortexing in 3 mL/gm of 10 mM Tris-HCl, pH 7. 4, and the suspension was allowed to incubate at 25° C. for 15 min. Following centrifugation at 31000 g for 15 min, the pellets were-resuspended by gentle Potter-Elvehjem homogenization to a final volume of 1.53 mL/g in 10 mM Tris-HCl, pH 7.4. Aliquots were stored at −80° C. until use. Protein concentration was determined by the method of Lowry et al. [Lowry et al, *J. Biol. Chem.*, 19, 265–271, 1951] using bovine serum albumin (BSA) as standard.

To prepare rat brain crude $P_2$ membranes, male Sprague-Dawley rats (150–200 g, Charles River, Boston, Mass.) were sacrificed by decapitation. Brains (minus. cerebella) were then treated as described above.

Each compound was initially screened at concentrations of 10, 100, and 1000 nM in order to obtain an estimate of sigma binding affinity and to determine the appropriate concentration range to use in 12-point competition curves. For most compounds in the study, a concentration range of 0.0005–100 nM was appropriate. A range of 0.005–1000 nM or 0.05–10,000 nM was used for the less potent compounds. Twelve concentrations of unlabeled ligand were incubated with 3 nM [$^3$H](+)-pentazocine as described previously [de Costa et al, *FEBS* Lett., 251, 53–58, 1989]. The CDATA iterative curve-fitting program (EMF Software, Inc., Baltimore, Md.) was used to determine $IC_{50}$ values. Values are the average of 2–4 experiments ± SEM. Each experiment was carried out in duplicate., The Cheng-Prussoff equation [Cheng, Y. -C. and Prusoff, W. H., *Biochem. Pharmacol.*, 3099–3108, 1973] was then used to convert $IC_{50}$ values to apparent $K_i$ values. The $K_d$ for [$^3$H]-(+)-pentazocine (4.8 nM) was determined in independent experiments using guinea pig brain membranes.

Sigma receptors were labeled with [$^3$H]-(+)-pentazocine (Specific activity =51.7 Ci/mmol). Incubations were carried out in 50 mM Tris-HCl, pH 8.0, for 120 min at 25° C. in a volume of 0.5 mL with 500 µg of membrane protein and 3 nM [$^3$H]-(+)-pentazocine. Nonspecific binding was determined in the presence of 10 µM (+)-pentazocine. Assays were terminated by the addition of 5 mL of ice-cold 10 mM Tris-HCl, pH 8.0, and filtration through glass-fiber filters (Schleicher and Schuell). Filters were then washed twice with 5 mL of ice-cold Tris-HCl buffer. Filters were soaked in. 0.5% polyethylenimine for at least 30 min at 25° C. prior to use.

TABLE II

| Test Compound | Ki ([3H] (+)-Pent) nM |
| --- | --- |
| Compound of Ex. 6 | 969.83 |
| Compound of Ex. 12 | 3.67 |
| Compound of Ex. 17 | 0.77 |

Also embraced within this invention is a class of pharmaceutical compositions comprising one or more compounds of Formula I in association with one or more non-toxic, pharmaceutically-acceptable carriers and/or diluents and/or adjuvants (collectively referred to herein as "carrier" materials) and, if desired, other active ingredients. The compounds of the present invention may be administered by any suitable route, preferably in the form a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical compositions may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogramof body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid; magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, aqueous sodium chloride, and/or various buffers. Other adjuvants and modes of administration are well and widely known in the pharmaceutical art.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of the formula:

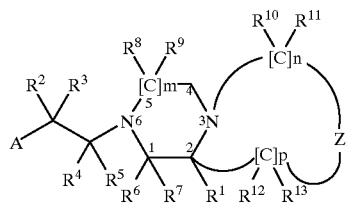

wherein each of $R^1$, $R^4$, and $R^5$ is independently selected from the group consisting of hydrido, alkyl, cycloalkyl, cycloalkylalkyl, aralkyl, aryl, alkoxyalkyl, haloalkyl, hydroxyalkyl, carboxy, carboxyalkyl, alkanoyl, alkenyl, and alkynyl; wherein $R^6$ and $R^7$ are hydrogen; wherein $R^2$ is selected from the group consisting of alkyl, cycloalkyl, cycloalkylalkyl, aryl, alkoxy, aryloxy, aralkoxy, alkoxyalkyl, haloalkyl, hydroxyalkyl, cyano, amino, monoalkylamino, dialkylamino, carboxy, carboxyalkyl, alkanoyl, alkenyl, and alkynyl; wherein each of $R^3$ and $R^8$ through $R^{13}$ is independently selected from the group consisting of hydrido, hydroxy, alkyl, cycloalkyl, cycloalkylalkyl, aralkyl, aryl, alkoxy, aryloxy, aralkoxy, alkoxyalkyl, haloalkyl, hydroxyalkyl, cyano, amino, monoalkylamino, dialkylamino, carboxy, carboxyalkyl, alkanoyl, alkenyl, and alkynyl; wherein $R^2$ and $R^3$ may be taken together to form oxo or may be taken together with the carbon to which they are attached to form a saturated or partially unsaturated carbocyclic group having three to eight ring carbons; wherein $R^4$ and $R^5$ may be taken together to form oxo or may be taken together with the carbon to which they are attached to form a saturated or partially unsaturated carbocyclic group having three to eight ring carbons; wherein $R^8$ and $R^9$ may be taken together to form oxo; wherein $R^{10}$ and $R^{11}$ may be taken together to form oxo; wherein m is equal to one; wherein Z is selected from the group consisting of

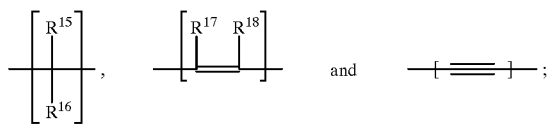

wherein each of $R^{15}$ and $R^{16}$ is independently selected from the group consisting of hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, amino, monoalkylamino, dialkylamino, carboxy, carboxyalkyl and alkanoyl; wherein each of $R^{17}$ and $R^{18}$ is independently selected from the group consisting of hydrido, alkyl, cycloalkyl, cycloalkylalkyl, aralkyl, alkoxyalkyl, haloalkyl, hydroxyalkyl, halo, cyano, carboxy, carboxyalkyl and alkanoyl; wherein when Z is

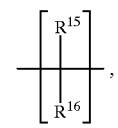

n and p are one or two, with a sum of two or three, and when Z is

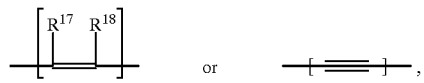

n and p are each one; wherein A is selected from the group consisting of aryl, heteroaryl, aryloxy, heteroaryloxy, aralkoxy, heteroaralkoxy, arylamino, heteroarylamino, aralkylamino, heteroaralkylamino, arylthio, heteroarylthio, aralkylthio, and heteroaralkylthio; wherein A can be further substituted with one or more substituents independently selected from the group consisting of hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, cyano, amino, monoalkylamino, dialkylamino, carboxy, carboxyalkyl, alkanoyl, alkenyl, and alkynyl; or a pharmaceutically acceptable salt thereof; with the proviso that when n and p both are 1, $R^4$ and $R^5$ are not alkyl, and at least one of $R^4$ and $R^5$ is not hydrogen.

2. The compound of claim 1 of the formula:

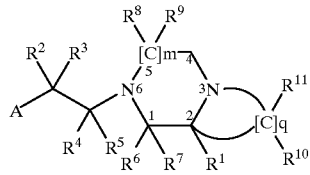

wherein each of $R^1$, $R^4$, and $R^5$ is independently selected from the group consisting of hydrido, loweralkyl, benzyl and haloloweralkyl; wherein $R^2$ is selected from the group consisting of alkyl, cycloalkyl, cycloalkylalkyl, aryl, alkoxy, aryloxy, aralkoxy, alkoxyalkyl, haloalkyl, hydroxyalkyl, cyano, amino, monoalkylamino, dialkylamino, carboxy, carboxyalkyl, alkanoyl, alkenyl, and alkynyl; wherein each of $R^3$ and $R^8$ through $R^{11}$ is independently selected from the group consisting of hydrido, hydroxy, loweralkyl, benzyl, phenoxy, benzyloxy and haloloweralkyl; wherein q is four; wherein m is one; wherein A is selected from the group consisting of phenyl, naphthyl, benzothienyl, benzofuranyl and thienyl; wherein any of the foregoing A groups can be further substituted with one or more substituents independently selected from the group consisting of hydrido, hydroxy, loweralkyl, loweralkoxy, halo, haloloweralkyl, amino, monoloweralkylamino and diloweralkylamino; or a pharmaceutically acceptable salt thereof.

3. A compound of the formula:

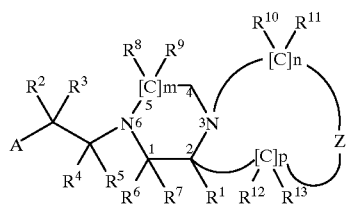

wherein each of $R^1$, $R^4$, and $R^5$ is independently selected from the group consisting of hydrido, alkyl, cycloalkyl, cycloalkylalkyl, aralkyl, aryl, alkoxyalkyl, haloalkyl, hydroxyalkyl, carboxy, carboxyalkyl, alkanoyl, alkenyl, and alkynyl; wherein $R^6$ and $R^7$ are hydrogen; wherein each of $R^2$, $R^3$, $R^8$, $R^9$, and $R^{11}$ through $R^{13}$ is independently selected from the group consisting of hydrido, hydroxy, alkyl, cycloalkyl, cycloalkylalkyl, aralkyl, aryl, alkoxy, aryloxy, aralkoxy, alkoxyalkyl, haloalkyl, hydroxyalkyl, cyano, amino, monoalkylamino, dialkylamino, carboxy, carboxyalkyl, alkanoyl, alkenyl, and alkynyl;wherein $R^{10}$ is selected from the group consisting of hydroxy, alkyl, cycloalkyl, cycloalkylalkyl, aralkyl, aryl, alkoxy, aryloxy, aralkoxy, alkoxyalkyl, haloalkyl, cyano, amino, monoalkylamino, dialkylamino, carboxy, carboxyalkyl, alkanoyl, alkenyl, and alkynyl;wherein $R^2$ and $R^3$ may be taken together to form oxo or may be taken together with the carbon to which they are attached to form a saturated or partially unsaturated carbocyclic group having three to eight ring carbons; wherein $R^4$ and $R^5$ may be taken together to form oxo or may be taken together with the carbon to which they are attached to form a saturated or partially unsaturated carbocyclic group having three to eight ring carbons; wherein $R^8$ and $R^9$ may be taken together to form oxo; wherein $R^{10}$ and $R^{11}$ may be taken together to form oxo; wherein m is equal to one; wherein Z is selected from the group consisting of

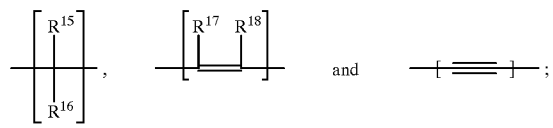

wherein each of $R^{15}$ and $R^{16}$ is independently selected from the group consisting of hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, amino, monoalkylamino, dialkylamino, carboxy, carboxyalkyl and alkanoyl; wherein each of $R^{17}$ and $R^{18}$ is independently selected from the group consisting of hydrido, alkyl, cycloalkyl, cycloalkylalkyl, aralkyl, alkoxyalkyl, haloalkyl, hydroxyalkyl, halo, cyano, carboxy, carboxyalkyl and alkanoyl; wherein when Z is

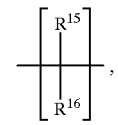

n and p are one or two, with a sum of two or three, and when Z is

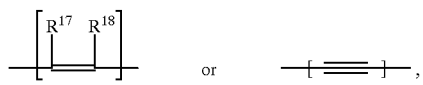

n and p are each one; wherein A is selected from the group consisting of aryl, heteroaryl, aryloxy, heteroaryloxy, aralkoxy, heteroaralkoxy, arylamino, heteroarylamino, aralkylamino, heteroaralkylamino, arylthio, heteroarylthio, aralkylthio, and heteroaralkylthio; wherein A can be further substituted with one or more substituents independently selected from the group consisting of hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, cyano, amino, monoalkylamino, dialkylamino, carboxy, carboxyalkyl, alkanoyl, alkenyl, and alkynyl; or a pharmaceutically acceptable salt thereof; with the proviso that when n and p both are 1, $R^4$ and $R^5$ are not alkyl, and at least one of $R^4$ and $R^5$ is not hydrogen.

4. The compound of claim 1, wherein neither $R^8$ and $R^9$, nor $R^{10}$ and $R^{11}$ are taken together to form oxo, and wherein each of $R^{15}$ and $R^{16}$ is independently selected from the group consisting of hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, carboxy, carboxyalkyl and alkanoyl; or a pharmaceutically acceptable salt thereof.

5. The compound of claim 4, wherein each of $R^1$, $R^4$, $R^5$, $R^6$ and $R^7$ is independently selected from the group consisting of hydrido, loweralkyl, cycloalkyl of three to eight carbon atoms, cycloalkylalkyl of four to eight carbon atoms, phenylloweralkyl, phenyl, loweralkoxyloweralkyl, haloloweralkyl, hydroxyloweralkyl, carboxy, carboxyloweralkyl, loweralkanoyl, loweralkenyl, and loweralkynyl; wherein each of $R^2$, $R^3$ and $R^8$ through $R^{13}$ is independently selected from the group consisting of hydrido, hydroxy, loweralkyl, cycloalkyl of three to eight carbon atoms, cycloalkylalkyl of four to eight carbon atoms, phenylloweralkyl, phenyl, loweralkoxy, phenoxy, phenylloweralkoxy, loweralkoxyloweralkyl, haloloweralkyl, hydroxyloweralkyl, cyano, amino, monoloweralkylamino, diloweralkylamino, carboxy, carboxyloweralkyl, loweralkanoyl, loweralkenyl and loweralkynyl; wherein each of $R^{15}$ and $R^{16}$ is independently selected from the group consisting of hydrido, hydroxy, loweralkyl, cycloalkyl of three to about eight carbon atoms, cycloalkylalkyl of four to eight carbon atoms, phenyloweralkyl, phenyl, loweralkoxyloweralkyl, haloloweralkyl, hydroxyloweralkyl, halo, cyano, carboxy, carboxyloweralkyl and loweralkanoyl; wherein each of $R^{17}$ and $R^8$ is selected from the group consisting of hydrido, loweralkyl, cycloalkyl of three to about eight carbon atoms, cycloalkylalkyl of four to eight carbon atoms, phenyloweralkyl, phenyl, loweralkoxyloweralkyl, haloloweralkyl, hydroxyloweralkyl, halo, cyano, carboxy, carboxyloweralkyl and loweralkanoyl; wherein A is selected from the group consisting of phenyl, naphthyl, heteroaryl, phenoxy, naphthyloxy, heteroaryloxy, phenylloweralkoxy, naphthylloweralkoxy, heteroarylloweralkoxy, phenylamino, naphthylamino, heteroarylamino, phenylloweralkylamino, naphthylloweralkylamino, heteroaralkylamino, phenylthio, naphthylthio, heteroarylthio, phenylloweralkylthio and heteroarylloweralkylthio; and wherein any of the foregoing A groups can be further substituted with one or more substituents independently selected from the group consisting of hydrido, hydroxy, loweralkyl, cycloalkyl of three to eight carbon atoms, cycloalkylalkyl of four to eight carbon atoms, phenylloweralkyl, phenyl, loweralkoxy, phenoxy, phenyloweralkoxy, loweralkoxyloweralkyl, halo, haloloweralkyl, hydroxyloweralkyl, cyano, amino, monoloweralkylamino, diloweralkylamino, carboxy, carboxyloweralkyl, loweralkanoyl, loweralkenyl and loweralkynyl; or a pharmaceutically acceptable salt thereof.

6. The compound of claim 5, wherein each of $R^1$, $R^4$, $R^5_1$, $R^6$ and $R^7$ is independently selected from the group consisting of hydrido, loweralkyl, cycloalkyl of three to eight carbon atoms, cycloalkylalkyl of four to eight carbon atoms, benzyl, phenyl, loweralkoxyloweralkyl, haloloweralkyl, hydroxyloweralkyl, loweralkanyol, loweralkenyl, and loweralkynyl; wherein each of $R^2$, $R^3$ and $R^8$ through $R^{13}$ is independently selected from the group consisting of hydrido, hydroxy, loweralkyl, cycloalkyl of three to about eight carbon atoms, cycloalkylalkyl of four to eight carbon atoms, benzyl, phenyl, loweralkoxy, phenoxy, benzyloxy, loweralkoxyloweralkyl, haloloweralkyl, hydroxyloweralkyl, loweralkanoyl, loweralkenyl and loweralkynyl; wherein each of $R^{15}$ through $R^{18}$ is independently selected from the group consisting of hydrido, loweralkyl, cycloalkyl of three to eight carbon atoms, cycloalkylalkyl of four to about eight carbons atoms, benzyl, phenyl, loweralkoxyloweralkyl, hydroxyloweralkyl and halo; wherein A is selected from the group consisting of phenyl, naphthyl, benzo [b]thienyl, thienyl, phenoxy, naphthyloxy, thiophenoxy, benzyloxy, phenylamino, naphthylamino, phenylthio, benzylamino, benzylthio and napthylthio; and wherein A can be further substituted with one or more substituents independently selected from the group consisting of hydrido, hydroxy, loweralkyl, cycloalkyl of three to eight carbon atoms, cycloalkylalkyl of four to eight carbon atoms, loweralkoxy, loweralkoxyloweralkyl, halo, haloloweralkyl, hydroxyloweralkyl, amino, monoloweralkylamino, diloweralkylamino, loweralkanoyl, loweralkenyl and loweralkynyl; or a pharmaceutically acceptable salt thereof.

7. The compound of claim 2, wherein each of said loweralkyls is selected from the group consisting of methyl, ethyl, and propyl; wherein A is phenyl or naphthyl; wherein either of the foregoing A groups can be further substituted with one or more substituents independently selected from the group consisting of hydroxy, methyl, ethyl, propyl, methoxy, ethoxy, methylenedioxy, halo, trifluoromethyl, amino, methylamino and dimethylamino; or a pharmaceutically acceptable salt thereof.

8. A pharmaceutical composition comprising:
(a) a compound of the formula:

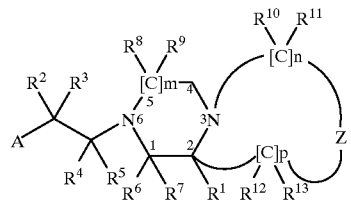

wherein each of $R^1$, $R^4_1$ and $R^5$ is independently selected from the group consisting of hydrido, alkyl, cycloalkyl, cycloalkylalkyl, aralkyl, aryl, alkoxyalkyl, haloalkyl, hydroxyalkyl, carboxy, carboxyalkyl, alkanoyl, alkenyl, and alkynyl; wherein $R^6$ and $R^7$ are hydrogen; wherein each of $R^2$, $R^3$, and $R^8$ through $R^{13}$ is independently selected from the group consisting of hydrido, hydroxy, alkyl, cycloalkyl, cycloalkylalkyl, aralkyl, aryl, alkoxy, aryloxy, aralkoxy, alkoxyalkyl, haloalkyl, hydroxyalkyl, cyano, amino, monoalkylamino, dialkylamino, carboxy, carboxyalkyl, alkanoyl, alkenyl, and alkynyl; wherein $R^2$ and $R^3$ may be taken together to form oxo or may be taken together with the carbon to which they are attached to form a saturated or partially unsaturated carbocyclic group having three to eight ring carbons; wherein $R^4$ and $R^5$ may be taken together to form oxo or may be taken together with the carbon to which they are attached to form a saturated or partially unsaturated carbocyclic group having three to eight ring carbons; wherein $R^8$ and $R^9$ may be taken together to form oxo; wherein $R^{10}$ and $R^{11}$ may be taken together to form oxo; wherein m is equal to one; wherein Z is selected from the group consisting of

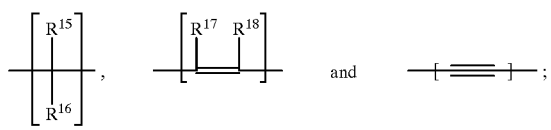

wherein each of $R^{15}$ and $R^{16}$ is independently selected from the group consisting of hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, amino, monoalkylamino, dialkylamino, carboxy, carboxyalkyl and alkanoyl; wherein each of $R^{17}$ and $R^{18}$ is independently selected from the group consisting of hydrido, alkyl, cycloalkyl, cycloalkylalkyl, aralkyl, alkoxyalkyl, haloalkyl, hydroxyalkyl, halo, cyano, carboxy, carboxyalkyl and alkanoyl; wherein when Z is

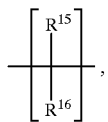

n and p are one or two, with a sum of two or three, and when Z is

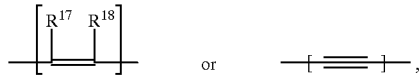

n and p are each one; wherein A is selected from the group consisting of aryl, heteroaryl, aryloxy, heteroaryloxy, aralkoxy, heteroaralkoxy, arylamino, heteroarylamino, aralkylamino, heteroaralkylamino, arylthio, heteroarylthio, aralkylthio, and heteroaralkylthio; wherein A can be further substituted with one or more substituents independently selected from the group consisting of hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, cyano, amino, monoalkylamino, dialkylamino, carboxy, carboxyalkyl, alkanoyl, alkenyl, and alkynyl; or a pharmaceutically acceptable salt thereof in an amount that is therapeutically-effective for treating or preventing a CNS-related disorder selected from the group consisting of ischemia and psychotic disorders, and (b) a pharmaceutically-acceptable carrier or diluent.

9. The pharmaceutical composition of claim 8, wherein wherein neither $R^8$ and $R^9$, nor $R^{10}$ and $R^{11}$ are taken together to form oxo, and wherein each of $R^{15}$ and $R^{16}$ is independently selected from the group consisting of hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, carboxy, carboxyalkyl and alkanoyl; or a pharmaceutically acceptable salt thereof.

10. The pharmaceutical composition of claim 9, wherein each of $R^1$, $R^4$, and $R^5$ is independently selected from the group consisting of hydrido, loweralkyl, cycloalkyl of three to eight carbon atoms, cycloalkylalkyl of four to eight carbon atoms, phenylloweralkyl, phenyl, loweralkoxyloweralkyl, haloloweralkyl, hydroxyloweralkyl, carboxy, carboxyloweralkyl, loweralkanoyl, loweralkenyl, and loweralkynyl; wherein each of $R^2$, $R^3$ and $R^8$ through $R^{13}$ is independently selected from the group consisting of hydrido, hydroxy, loweralkyl, cycloalkyl of three to eight carbon atoms, cycloalkylalkyl of four to eight carbon atoms, phenylloweralkyl, phenyl, loweralkoxy, phenoxy, phenylloweralkoxy, loweralkoxyloweralkyl, haloloweralkyl, hydroxyloweralkyl, cyano, amino, monoloweralkylamino, diloweralkylamino, carboxy, carboxyloweralkyl, loweralkanoyl, loweralkenyl and loweralkynyl; wherein each of $R^{15}$ and $R^{16}$ is independently selected from the group consisting of hydrido, hydroxy, loweralkyl, cycloalkyl of three to about eight carbon atoms, cycloalkylalkyl of four to eight carbon atoms, phenylloweralkyl, phenyl, loweralkoxyloweralkyl, haloloweralkyl, hydroxyloweralkyl, halo, cyano, carboxy, carboxyloweralkyl and loweralkanoyl; wherein each of $R^{17}$ and $R^{18}$ is selected from the group consisting of hydrido, loweralkyl, cycloalkyl of three to about eight carbon atoms, cycloalkylalkyl of four to eight carbon atoms, phenylloweralkyl, phenyl, loweralkoxyloweralkyl, haloloweralkyl, hydroxyloweralkyl, halo, cyano, carboxy, carboxyloweralkyl and loweralkanoyl; wherein A is selected from the group consisting of phenyl, naphthyl, heteroaryl, phenoxy, naphthyloxy, heteroaryloxy, phenylloweralkoxy, naphthylloweralkoxy, heteroarylloweralkoxy, phenylamino, naphthylamino, heteroarylamino, phenylloweralkylamino, naphthylloweralkylamino, heteroaralkylamino, phenylthio, naphthylthio, heteroarylthio, phenylloweralkylthio and heteroarylloweralkylthio; and wherein any of the foregoing A groups can be further substituted with one or more substituents independently selected from the group consisting of hydrido, hydroxy, loweralkyl, cycloalkyl of three to eight carbon atoms, cycloalkylalkyl of four to eight carbon atoms, phenylloweralkyl, phenyl, loweralkoxy, phenoxy, phenylloweralkoxy, loweralkoxyloweralkyl, halo, haloloweralkyl, hydroxyloweralkyl, cyano, amino, monoloweralkylamino, diloweralkylamino, carboxy, carboxyloweralkyl, loweralkanoyl, loweralkenyl and loweralkynyl; or a pharmaceutically acceptable salt thereof.

11. The pharmaceutical composition of claim 10, wherein each of $R^1$, $R^4$, and $R^5$ is independently selected from the group consisting of hydrido, loweralkyl, cycloalkyl of three to eight carbon atoms, cycloalkylalkyl of four to eight carbon atoms, benzyl, phenyl, loweralkoxyloweralkyl, haloloweralkyl, hydroxyloweralkyl, loweralkanyol, loweralkenyl, and loweralkynyl; wherein each of $R^2$, $R^3$ and $R^8$ through $R^3$ is independently selected from the group consisting of hydrido, hydroxy, loweralkyl, cycloalkyl of three to about eight carbon atoms, cycloalkylalkyl of four to eight carbon atoms, benzyl, phenyl, loweralkoxy, phenoxy, benzyloxy, loweralkoxyloweralkyl, haloloweralkyl, hydroxyloweralkyl, loweralkanoyl, loweralkenyl and loweralkynyl; wherein each of $R^{15}$ through $R^{13}$ is independently selected from the group consisting of hydrido, loweralkyl, cycloalkyl of three to eight carbon atoms, cycloalkylalkyl of four to about eight carbons atoms, benzyl, phenyl, loweralkoxyloweralkyl, hydroxyloweralkyl and halo; wherein A is selected from the group consisting of phenyl, naphthyl, benzo[b]thienyl, thienyl, phenoxy, naphthyloxy, thiophenoxy, benzyloxy, phenylamino, naphthylamino, phenylthio, benzylamino, benzylthio and napthylthio; and wherein A can be further substituted with one or more substituents independently selected from the group consisting of hydrido, hydroxy, loweralkyl, cycloalkyl of three to eight carbon atoms, cycloalkylalkyl of four to eight carbon atoms, loweralkoxy, loweralkoxyloweralkyl, halo, haloloweralkyl, hydroxyloweralkyl, amino, monoloweralkylamino, diloweralkylamino, loweralkanoyl, loweralkenyl and loweralkynyl; or a pharmaceutically acceptable salt thereof.

12. The pharmaceutical composition of claim 11, wherein said compound is of the formula:

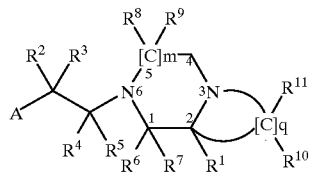

wherein each of $R^1$, $R^4$, and $R^5$ is independently selected from the group consisting of hydrido, loweralkyl, benzyl and haloloweralkyl; wherein each of $R^2$, $R^3$ and $R^8$ through $R^{11}$ is independently selected from the group consisting of hydrido, hydroxy, loweralkyl, benzyl, phenoxy, benzyloxy and haloloweralkyl; wherein q is four; wherein A is selected from the group consisting of phenyl, naphthyl, benzothienyl, benzofuranyl and thienyl; wherein any of the foregoing A groups can be further substituted with one or more substituents independently selected from the group consisting of hydrido, hydroxy, loweralkyl, loweralkoxy, halo, haloloweralkyl, amino, monoloweralkylamino and diloweralkylamino; or a pharmaceutically acceptable salt thereof.

13. The pharmaceutical composition of claim 12, wherein each of said loweralkyls is selected from the group consisting of methyl, ethyl, and propyl; wherein A is phenyl or naphthyl; wherein either of the foregoing A groups can be further substituted with one or more substituents independently selected from the group consisting of hydroxy, methyl, ethyl, propyl, methoxy, ethoxy, methylenedioxy, halo, trifluoromethyl, amino, methylamino and dimethylamino; or a pharmaceutically acceptable salt thereof.

14. A method of treating a mammal for a CNS-related disorder selected from the group consisting of ischemia and psychotic disorders, which method comprises administering to the mammal a therapeutic effective amount of the pharmaceutical composition of claim 8.

15. A method of treating a mammal for a CNS-related disorder selected from the group consisting of ischemia and psychotic disorders, which method comprises administering to the mammal a therapeutical-effective amount of the pharmaceutical composition of claim 9.

16. A method of treating a mammal for a CNS-related disorder selected from the group consisting of ischemia and psychotic disorders, which method comprises administering to the mammal a therapeutically-effective amount of the pharmaceutical composition of claim 10.

17. A method of treating a mammal for a CNS-related disorder selected from the group consisting of ischemia and psychotic disorders, which method comprises administering to the mammal a therapeutically-effective amount of the pharmaceutical composition of claim 11.

18. A method of treating a mammal for a CNS-related disorder selected from the group consisting of ischemia and psychotic disorders, which method comprises administering to the mammal a therapeutic effective amount of the pharmaceutical composition of claim 12.

19. A method of treating a mammal for a CNS-related disorder selected from the group consisting of ischemia and psychotic disorders, which method comprises administering to the mammal a therapeutically-effective amount of the pharmaceutical composition of claim 13.

20. The method of claim 14, wherein said CNS-related disoder is cerebral ischemia.

21. The method of claim 14, wherein said CNS-related disorder is a psychotic disorder.

* * * * *